(12) United States Patent
Barillon et al.

(10) Patent No.: US 8,389,940 B2
(45) Date of Patent: Mar. 5, 2013

(54) DISCRIMINATING MOLECULE FAMILY FOR NEUTRON AND GAMMA RADIATION

(75) Inventors: Remi Barillon, Marlenheim (FR); Ezeddine Bouajila, Villeurbanne (FR); Laurent Douce, Strasbourg (FR); Jean-Marc Jung, Gougenheim (FR); Louise Stuttge, Strasbourg (FR)

(73) Assignee: Universite Louis Pasteur de Strasbourg, Strasbourg (FR)

( * ) Notice: Subject to any disclaimer, the term of this patent is extended or adjusted under 35 U.S.C. 154(b) by 20 days.

(21) Appl. No.: 13/003,646

(22) PCT Filed: Jul. 10, 2009

(86) PCT No.: PCT/FR2009/051382
§ 371 (c)(1),
(2), (4) Date: Sep. 1, 2011

(87) PCT Pub. No.: WO2010/004228
PCT Pub. Date: Jan. 14, 2010

(65) Prior Publication Data
US 2011/0303850 A1    Dec. 15, 2011

(30) Foreign Application Priority Data
Jul. 11, 2008    (FR) .................................... 08 54740

(51) Int. Cl.
    *G01T 1/10*    (2006.01)

(52) U.S. Cl. ...................................................... 250/362
(58) Field of Classification Search ................... 250/362
    See application file for complete search history.

(56) References Cited

PUBLICATIONS

Adhikari et al., "Polymers in sensor applications," 2004, Progress in Polymber Science, vol. 29, pp. 699-766.*
International Search Report and the Written Opinion from corresponding PCT Application No. PCT/FR2009/051382, dated Jan. 22, 2010.
Meyer et al., "Water-Binding Solid Scintillators: Synthesis, Emission Properties, and Tests in 3H and 14C Counting," Chem. Eur. J., 6:2809-2817 (2000).
McCairn et al., "Synthesis, Evaluation and Incorporation into Liposomes of 4-Functionalised-2,5- Diphenyloxazole Derivatives for Application in Scintillation Proximity Assays," Tetrahedron Letters, 45:2163-2166 (2004).
Katritzky et al. "Synthesis of Fluorescent and Coloured Pyrylium and Pyridinium Salts," J. Heterocyclic Chem., 21:1673-1677 (1984).

* cited by examiner

*Primary Examiner* — Kiho Kim
(74) *Attorney, Agent, or Firm* — McDermott Will & Emery

(57) ABSTRACT

The invention relates to a novel discriminating molecule family for neutron and gamma radiation, and to the preparation method thereof. Said molecules are also useful for detecting radiation (X, gamma, electrons, protons, ions), and thus for manufacturing radar, and industrial or medical dosimetry instruments.

28 Claims, 5 Drawing Sheets

DISCRIMINATING MOLECULE FAMILY FOR NEUTRON AND GAMMA RADIATION

RELATED APPLICATIONS

Figure 1:
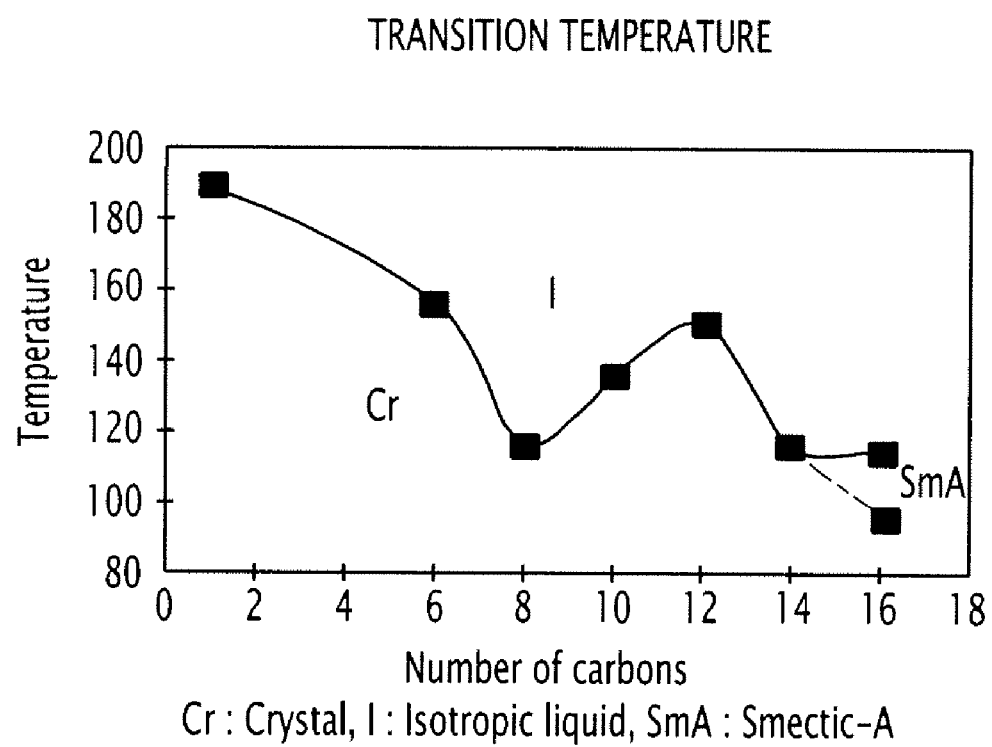

This application is the U.S. National Stage of International Application No. PCT/FR2009/051382, filed Jul. 10, 2009, which claims the benefit of French Application Serial No. 0854740, filed Jul. 11, 2008.

The present invention concerns a novel family of molecules discriminating between neutron radiation and gamma radiation in particular, and a method for the preparation thereof. These molecules can also be used for the detection of nuclear radiation, in fundamental research or in the fields of dosimetry and medical imaging.

The production of electron-hole pairs by ionization forms the first step, one of the most rapid, in the relaxation of energy initially deposited by radiation in a medium. In the excited organic matter, the formed pairs generally consist of a near-free electron in the conduction band, geminate (electrically paired) with a hole that is much less mobile in the valence band.

Discrimination is based on the fact that the quantity of energy, dE, deposited in a medium per unit of distance travelled, dx, by incident radiation, is different depending on whether this radiation is formed of photons or of charged particles. With excitation by gamma photons derived for example from a radioactive source, the quantity dE/dx is relatively small, which implies low ionization densities, and hence a relatively low production of electron-hole pairs. With excitation by neutrons, different nuclear reactions occur, the most important being the (n,p) reaction during which a proton (p) is ejected from a nucleus by elastic collision with an incident neutron (n). This proton will naturally slow down in the medium through excitation and ionization of the latter, producing geminate electron-hole pairs of the same type as those produced with gamma radiation, but with much stronger ionization density.

The deferred recombining of the produced pairs being the cause of fluorescence emission, such emission will be more intense with excitation by neutrons (indirectly by protons) than by gamma photons. The comparison between the fluorescence intensities emitted during the two types of excitation, photons and neutrons, therefore allows discrimination.

Discrimination between neutron radiation and gamma radiation is generally performed using three types of methods:

by measuring the time-of-flight of gamma particles and neutrons;
through the use of semiconductor detectors; or
through the use of scintillating molecules diluted in transparent plastic materials.

The method which consists of measuring times-of-flight is particularly complex to implement at technical and operational level, notably on account of the difficulty in accessing good time reference. It effectively requires extensive technicality both in the material preparation of the experiment and in the conducting thereof. This technique, which nevertheless gives very accurate results, remains essentially dedicated to research laboratories and applications in a scarcely hostile medium.

The method which consists of using a semiconductor material as active part of a detector remains limited to strong fluences. In this field of application, the main limitation to the use of conductor materials always lies in the fact that measurement is made on the quantity of charges produced or the generated current. In all cases, measurements remain little sensitive since the detection limit of a current is in the region of a picoampere and therefore only corresponds to the production of around 10 million mobile charge carriers each second. The low sensitivity of this method is generally offset by an increase in the sensitive volume of the detector, but then new problems arise related to the global decrease in the conduction of the assembly and to degradation of the detector's time response.

Measurements based on scintillation of diluted molecules are by far those that are most used.

When the irradiated medium contains luminescent molecules, the geminate recombining of the electron-hole pairs resulting from primary ionization leads to deferred fluorescence emission, with a defined yield, whose intensity will be proportional to the density of the ionizations produced by the radiation on its pathway. This intensity is higher with the passing of a proton than with the passing of a photon on account of greater energy loss per unit of distance travelled dE/dx. Therefore, by measuring deferred fluorescence, it is possible to discriminate between fluorescence resulting from the passing of a proton [produced by a neutron during a (n,p) reaction] and fluorescence resulting from the passing of a photon. Comparison of the intensities of the two emitted fluorescence signals allows discrimination. The difficulty in measurement essentially results from the fact that fluorescence is only emitted during a very short time, a few hundred nanoseconds, after passing of the primary radiation, which implies specific instrumentation operating with nanosecond temporal resolution. Since the intensity of fluorescence is globally low, it can only be detected with the aid of photomultipliers. The fluorescence emission spectrum is independent of the type of excitation, and only depends on the type of chromophore chosen. The sensitivity of detection is much higher than the sensitivity that can be expected from current measurement, since only a few thousand free charge carriers need to be produced in the media for detection to become possible.

The diluted scintillating molecules are generally oxazoles or oxadiazoles, even para-terphenyl or anthracene. All these molecules have nanosecond luminescence properties in a spectral region ranging from 300 to 400 nm.

This method, based on the measurement of recombination fluorescence after interception of the charges produced in the medium by the scintillating molecules, is by far the most rapid (nanosecond) and the most sensitive. In theory, the production of a single free charge in the medium is sufficient to produce detectable fluorescence and hence measurement. The method then appears to be 10 million times more sensitive than the method based on conduction. However, under current practice, the fact that the dilution limit of a scintillating molecule in a plastic lies in the region of 0.01 mole/L, means that sensitivity is reduced by factor of 10 to 100. The other factor reducing sensitivity is given by the solid angle of light detection. This can be estimated at 100 to 1000. The use of photomultiplier having a typical detection yield of 20% therefore reduces sensitivity by a factor of about 5. Globally, it can be estimated that fluorescence techniques are about 1000 times more sensitive than electric techniques, and that the main limitation is due to the dilution of the fluorescent molecules. The use of non-diluted, aromatic fluorescent materials is possible, either in the liquid state (benzene, xylene), or in the solid state (p-terphenyl, anthracene). These materials are highly flammable and toxic however. For example benzene, and xylene used commercially under the trade name Ne213, are intercalating agents, hence carcinogenic and mutagenic. They are also eye and skin irritants.

A novel family of fluorescent molecules radiation has now been discovered, also allowing real-time discrimination between neutron radiation and gamma radiation in particular. These molecules result from the combining of a fluorescent entity with an ionic entity comprising a heteroatom chosen from among N, S or P carrying a positive charge, for example an ionic entity of imidazolium type. Against all expectations, the compounds thus obtained firstly have rapid fluorescence properties (nanosecond) and emit in the ultraviolet (400 nm), and secondly have the properties of ionic liquids. The fact that these materials have at least one fluorophore group per molecule imparts substantial fluorescence yields, similar to those of non-diluted materials, but with numerous additional properties:

non-measurable vapour pressure, allowing high-vacuum use;

good thermal stability (200° C.);

non-flammable nature;

low toxicity;

liquid or solid state;

easier forming and machining;

liquid crystal properties.

In addition to these properties, the customized forming of molecules allows the efficacy of the initial interaction to be adjusted to radiation, to increase energy loss (dE/dx) and hence the quantity of emitted light. This can be obtained, for example, by adding a heavy atom (photon detection) or by increasing the number of hydrogen atoms (neutron detection). Improved detection sensitivity is obtained, in both pure and diluted media, insofar as the construction of the molecule and interaction parameters are better controlled.

Therefore, a first subject of the invention concerns the use for the detection of gamma, X, neutron, proton radiation of a fluorophore compound $F_1$ carrying an organic cationic group combined with a counter-anion, or else carrying an anionic group combined with an organic counter-cation, said cationic group or organic counter-cation comprising at least one heteroatom chosen from among N, S or P carrying a positive charge.

Preferably, the fluorophore compound $F_1$ carries an organic cationic group combined with a counter-anion.

Preferably, the organic cationic group is a heterocylic group optionally substituted by one to three groups chosen from among $R^{1a}$, $R^{1b}$, $R^{1c}$ or $R^{25}$, or else the organic cationic group is a group (a), (b), (c) or (d):

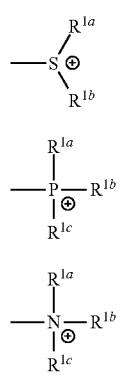

(a)

(b)

(c)

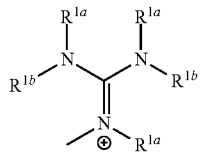

(d)

where $R^{1a}$, $R^{1b}$, $R^{1c}$ on each occurrence, are each independently chosen from among H, $C_1$-$C_{30}$ alkyl groups, $C_3$-$C_7$ cycloalkyl groups, $C_6$-$C_{10}$ aryl groups, heteroaryl, arylalkyl, heteroarylalkyl groups, a fluorophore group, in which said alkyl or aryl groups are optionally substituted by 1 to 3 $R^{20}$ groups;

$R^{25}$ is independently chosen from among OH, $NH_2$, =O, C(=O)$OR^{21}$;

$R^{20}$, on each occurrence, is independently chosen from among F, Cl, Br, I, $OR^{22}$, $NR^{23}R^{24}$, NHOH, $NO_2$, CN, $CF_3$, $C_1$-$C_6$ alkyl, $C_2$-$C_6$ alkenyl, $C_2$-$C_6$ alkynyl, $C_6$-$C_{10}$ aryl, arylalkyl, =O, C(=O)$R^{22}$, $CO_2R^{22}$, OC(=O)$R^{22}$, C(=O)$NR^{23}R^{24}$, OC(=O)$NR^{23}R^{24}$, $NR^{21}$C(=S)$R^{22}$ and S(O)$_y R^{22}$;

$R^{21}$ on each occurrence is independently chosen from among H or $C_1$-$C_6$ alkyl;

$R^{22}$ on each occurrence is independently chosen from among H, $C_1$-$C_6$ alkyl, $C_6$-$C_{10}$ aryl and arylalkyl;

$R^{23}$ and $R^{24}$ on each occurrence are independently chosen from among H, $C_1$-$C_6$ alkyl, $C_6$-$C_{10}$ aryl, or else $R^{23}$ and $R^{24}$ together with the hydrogen atom to which they are attached form a 3 to 7-membered heterocyclic group.

According to one preferred embodiment, the invention concerns the use of a compound of formula (A):

L*-Y—Z$^+$ $^-$X wherein:

$Z^+$ is an organic cationic group such as defined above, $X^-$ is an organic or inorganic anion, Y is a $C_1$-$C_6$ alkylene group, or ($C_1$-$C_4$ alkylene)$_m$-Q-($C_1$-$C_4$ alkylene)$_n$ group;

$C_6$-$C_{10}$ arylene group;

in which the alkylene, arylene groups are optionally substituted by 1 to 3 $R^{20}$ groups;

Q is a —C(=O)—, —$NR^{21}$C(=O)—, —C(=O)$NR^{21}$—, —C(=O)O—, —OC(=O)—, —O—, —$NR^{21}$—, —S(O)$_y$—, —$CR^{21}$=$CR^{21}$—, —C≡C—, $C_6$-$C_{10}$ arylene, 5 to 10-membered heteroarylene, $C_3$-$C_6$ cycloalkylene, or 3 to 6-membered heterocycloalkylene group, in which said arylene, heteroarylene, cycloalkylene groups are optionally substituted by 1 to 3 $R^{20}$ groups;

L* is a fluorophore group $F_1$, m is 0 or 1;

n is 0 or 1;

y is 0, 1 or 2, the $R^{20}$ and $R^{21}$ groups being such as defined above.

Preferably, the invention concerns the use of the above-defined fluorophores, for discriminating between proton/gamma, proton/X, neutron/gamma, neutron/X, alpha/gamma, alpha/X radiation.

Preferably, the organic cationic group is a heterocyclic group comprising at least one nitrogen atom. As examples of particularly preferred groups, particular mention may be made of the groups: pyridyl, imidazolyl, imidazolidinyl, oxazolyl, oxazolidinyl, thiazolyl, thiazolidinyl, pyrazolyl, triazolyl, tetrazolyl, benzotriazolyl, a guanine group or caprolactam group.

More preferably, the organic cationic group is chosen from among:

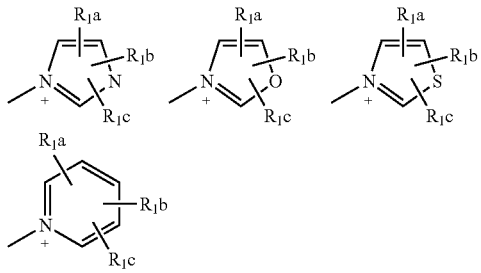

According to one particularly preferred embodiment, the organic cationic group is a pyridyl or imidazolyl group, notably:

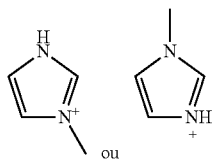

or

Preferably, the fluorophore compound $F_1$ carrying a cationic or anionic group is an oxazolyl, oxadiazolyl, anthracenyl or phenanthrenyl radical.

According to one preferred variant, the compounds which can be used according to the invention are of formula (I):

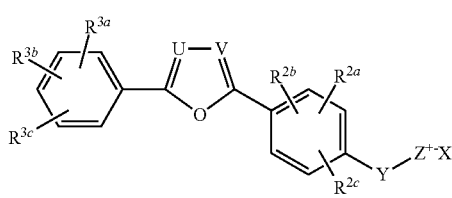

wherein:
U, V independently represent $CR^{26}$ or N, provided that at least one of U or V represents N;
$R^{26}$ is H, $C_1$-$C_6$ alkyl, $OR^{22}$, $NR^{23}R^{24}$, $NO_2$, $C(=O)R^{22}$, $CO_2R^{22}$, $OC(=O)R^{22}$, $C(=O)NR^{23}R^{24}$, $OC(=O)NR^{23}R^{24}$, $SO_3H$, $PO_4H$, CN.
$R^{2a}$, $R^{2b}$, $R^{2c}$, $R^{3a}$, $R^{3b}$, $R^{3c}$ on each concurrence are each independently chosen from among H, $C_1$-$C_{30}$ alkyl groups, $C_3$-$C_7$ cycloalkyl, $C_6$-$C_{10}$ aryl, heteroaryl, arylalkyl, heteroarylalkyl groups, in which said alkyl or aryl groups are optionally substituted by 1 to 3 $R^{20}$ groups;
Y, $Z^+$, $X^-$, $R^{20}$, $R^{22}$, $R^{23}$, $R^{24}$ being such as defined above.
More preferably, the compound of formula (A) is of formula (Ia):

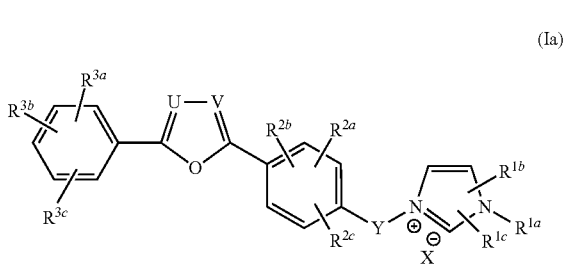

According to another aspect, the invention concerns the use of a fluorophore compound such as defined above, for the manufacture of radar and industrial or medical dosimetry instruments.

A second subject of the invention concerns a fluorophore compound carrying an organic cationic group combined with a counter-anion, or else an anionic group combined with an organic counter-cation, said cationic group or counter-cation comprising at least one heteroatom chosen from among N, S or P carrying a positive charge, in which the fluorophore group is not an anthracenyl group.

Preferably, the fluorophore is chosen from among an oxazolyl, oxadiazolyl or phenanthrenyl radical, and is more preferably an oxazolyl radical.

According to one preferred variant, the compounds of the invention are of formula (I):

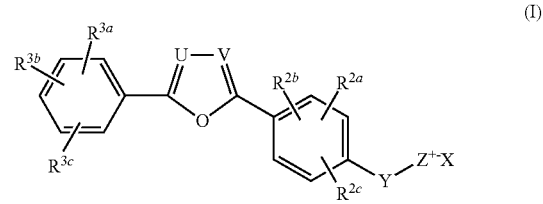

in which $Z^+$, $X^-$, Y, U, V, $R^{2a}$, $R^{2b}$, $R^{2c}$, $R^{3a}$, $R^{3b}$, $R^{3c}$ are all such as defined above.

More preferably, the compounds of the invention are of formula (Ia):

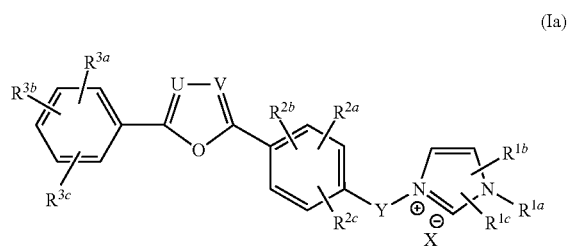

Preferably, $R^{1a}$ is a $C_1$-$C_{16}$ alkyl group.
Preferably, $R^{1b}$ and $R^{1c}$ are both H.
Preferably, U is $CR^{26}$, and notably CH.
According to one variant Y is a $C_1$-$C_6$ alkylene group, notably a $CH_2$ group.
Preferably, $X^-$ is an anion chosen from among a halide, $P(R^4)_6^-$, $B(R^4)_4^-$, $SCN^-$, $(R^5SO_2)_2N^-$, $R^5OSO_3^-$, $R^5SO_3^-$, carborane, carbonate $(CO_3^{2-})$, hydrogenocarbonate $(HCO_3^-)$, alcoholate $(R^4O^-)$, carboxylate $(R^4COO^-)$, amide $(NH_2^-)$, phosphate $(PO_4^-)$, $SiF_6^-$, $SbF_6^-$, $I_3^-$, nitrate $(NO_3^-)$, halide oxide, silicate, sulphate $(SO_4^-)$, sulphonate $(R^4SO_3^-)$, cyanide $(CN^-)$, carbanions, or metallate;
where:
$R^4$ on each occurrence is a group independently chosen from among a halogen atom, $C_1$-$C_6$ alkyl group, a $C_6$-$C_{10}$ aryl group, an arylalkyl group;
$R^5$ on each occurrence is a group independently chosen from among $C_1$-$C_{20}$ alkyl, $C_1$-$C_{20}$ halogenoalkyl, $C_6$-$C_{10}$ aryl, arylalkyl.

The term «metallate» designates an anionic complex containing a metal, notably a transition metal complexed with several ligands, for example a chalcogen such as oxygen or a cyanide group. Preferably, the metallate anion is a cyanometallate or oxometallate group.

The term «carborane» designates a molecule consisting of boron, carbon and hydrogen atoms and carrying a negative charge. For example, mention may be made of $CB_{11}H_{12}^-$.

The term «halide oxide» designates oxides of formula $HalO_x^-$ where Hal represents Br, Cl or I, and x is an integer of 1 to 4. As an example, mention may be made of $ClO_4^-$, $IO_3^-$.

The term «carbanion» designates a compound comprising a carbon atom carrying a negative charge. As an example, mention may be made of $(CF_3SO_2)_3C^-$.

More preferably, $X^-$ is chosen from among $Br^-$, $PF_6^-$, $BF_4^-$, $(CF_3SO_2)_2N^-$, $C_{12}H_{25}OSO_3^-$, $C_{16}H_{33}OSO_3^-$, $CF_3SO_3^-$.

Among the preferred compounds, particular mention may be made of:

1-methyl-3-[4-(5-phenyl-oxazol-2-yl)-benzyl]-3H-imidazol-1-ium bromide, 1-hexyl-3-[4-(5-phenyl-oxazol-2-yl)-benzyl]-3H-imidazol-1-ium bromide, 1-octyl-3-[4-(5-phenyl-oxazol-2-yl)-benzyl]-3H-imidazol-1-ium bromide, 1-decyl-3-[4-(5-phenyl-oxazol-2-yl)-benzyl]-3H-imidazol-1-ium bromide, 1-dodecyl-3-[4-(5-phenyl-oxazol-2-yl)-benzyl]-3H-imidazol-1-ium bromide, 3-[4-(5-phenyl-oxazol-2-yl)-benzyl]-1-tetradecyl-3H-imidazol-1-ium bromide, 1-hexadecyl-3-[4-(5-phenyl-oxazol-2-yl)-benzyl]-3H-imidazol-1-ium bromide, 1-hexadecyl-3-[4-(5-phenyl-oxazol-2-yl)-benzyl]-3H-imidazol-1-ium hexafluorophosphate, 1-hexadecyl-3-[4-(5-phenyl-oxazol-2-yl)-benzyl]-3H-imidazol-1-ium bis(trifluoromethylsulphonyl)imide, 1-hexadecyl-3-[4-(5-phenyl-oxazol-2-yl)-benzyl]-3H-imidazol-1-ium dodecyl sulphate, 1-hexadecyl-3-[4-(5-phenyl-oxazol-2-yl)-benzyl]-3H-imidazol-1-ium hexadecyl sulphate.

A further subject of the invention concerns a material, notably a transparent plastic material, comprising a compound such as defined above.

The compounds of the invention can be prepared by applying or adapting any method known per se and/or within the reach of persons skilled in the art, notably those described by Larock in *Comprehensive Organic Transformations*, VCH Pub., 1989, or by applying or adapting the methods described in the following examples.

The compounds of the invention can notably be prepared by causing a fluorophore compound carrying a leaving group to react with a group comprising a nucleophilic heteroatom chosen from among N, S or P, so as to form an organic cationic group such as defined above.

Therefore, according to one particular embodiment, the invention concerns a method for preparing a compound of formula (Ia) comprising the reaction of a compound of formula (II) with a compound of formula (III):

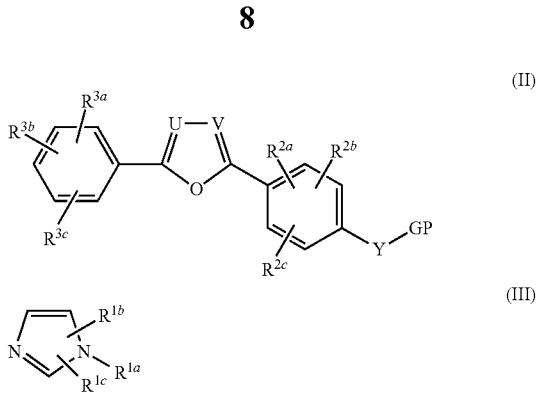

wherein $R^{1a}$, $R^{1b}$, $R^{1c}$, $R^{2a}$, $R^{2b}$, $R^{2c}$, $R^{3a}$, $R^{3b}$, $R^{3c}$, U and Y are such as defined above and GP represents a leaving group.

By «leaving group» is meant a labile chemical group i.e. which can easily be substituted by a nucleophilic group. As example of a leaving group, particular mention may be made of Cl, Br, I or the sulphonates such as mesylate or tosylate.

Optionally, said method may also comprise the step consisting of isolating the product obtained.

This reaction generally consists of second order substitution of the precursors of formulas (II) and (III). This reaction is generally conducted in a polar aprotic solvent, notably in an ether such as tetrahydrofuran. The compounds of general formulas (II) and (III) can be prepared by applying or adapting any method known per se and/or within the reach of persons skilled in the art, more particularly using the method described in the literature [1] or in [2 to 5] for the compounds of formula (III)).

The compounds of the invention can also be prepared from a fluorophore compound carrying a precursor group of a cationic group such as defined above, more precisely a group that is not electronically charged comprising a heteroatom chosen from among N, S or P. More particularly, the compounds of the invention can be prepared by causing said compound to react with an electrophilic compound, e.g. with an acid or an alkylating agent.

As a non-limiting illustration of this synthesis route, the following reaction scheme can be cited.

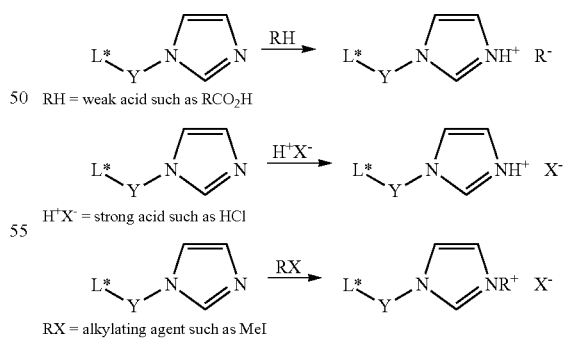

RH = weak acid such as $RCO_2H$ $H^+X^-$ = strong acid such as HCl

RX = alkylating agent such as MeI

L*, Y being such as defined in the present application

The compounds of the invention can also be prepared by adding an anionic group to the fluorophore compound, e.g. an anion carboxylate ($CO_2^-$) and combining this anion with an organic counter-cation comprising a heteroatom chosen from among N, S or P, said heteroatom carrying the positive charge.

The reaction scheme below is given by way of illustration of this synthesis route and is non-limiting:

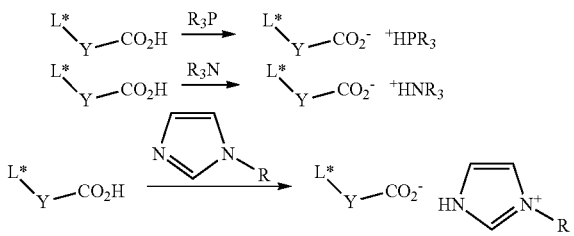

L*, Y being such as defined in the present application
Definitions

Such as used above and throughout the entire description of the invention, the following terms, unless indicated to the contrary, are to be construed as having the following meanings.

According to the present invention, the term « fluorophore » designates a fluorescent group, capable of absorbing energy at a specific wavelength and of re-emitting energy at a different but also specific wavelength. The quantity and wavelength of the re-emitted energy depend both on the fluorophore and on the chemical environment of the fluorophore.

According to the present invention, the alkyl radicals represent saturated hydrocarbon radicals, straight chain or branched, with 1 to 30 carbon atoms, preferably 1 to 20 carbon atoms. When they are linear, particular mention may be made of methyl, ethyl, propyl, butyl, pentyl, hexyl, octyl, nonyl, decyl, dodecyl, hexadecyl and octadecyl radicals.

When they are branched or substituted by one or more alkyl radicals, particular mention may be made of isopropyl, tert-butyl, 2-ethylhexyl, 2-methylbutyl, 2-méthylpentyl, 1-methyl pentyl and 3-methylheptyl radicals.

The term « halogenoalkyl » designates an alkyl radical substituted by one or more halogen atoms. The halogenalkyl radicals include the perhalogenoalkyl radicals and notably the perfluoroalkyl radicals of formula $CnF_{2n+1}$.

The term « halogen » designates a chlorine, bromine, iodine or fluorine atom.

The term « cycloalkyl » designates a non-aromatic, mono- or multicyclic ring with 3 to 10 carbon atoms, preferably 5 to 7 carbon atoms. As examples of monocyclic cycloalkyls, particular mention may be made of cyclopentyl, cyclohexyl, cycloheptyl, and similar. As examples of multicyclic cycloalkyl groups, 1-decaline, norbornyl, or adamant-(1 or 2-)yl can be particularly cited.

The term « alkenyl » designates an aliphatic hydrocarbon group which contains a double carbon-carbon bond and which may be straight or branched with 2 to 6 carbon atoms in the chain. Branched means that one or more lower alkyl groups such as methyl, ethyl or propyl, are bound to a linear alkenyl chain. As examples of alkenyl groups, particular mention may be made of ethenyl, propenyl, n-butenyl, i-butenyl, 3-methylbut-2-enyl, or n-pentenyl.

The term « alkynyl » designates an aliphatic hydrocarbon group which contains a triple carbon-carbon bond and which may be straight or branched with 2 to 6 carbon atoms in the chain, preferably 2 to 4 carbon atoms. Branched means that one or more lower alkyl groups, such as methyl, ethyl or propyl, are bound to a linear alkynyl chain. As examples of alkynyl groups, mention may notably be made of ethynyl, propynyl, n-butynyl, 2-butynyl, 3-methylbutynyl, and n-pentynyl.

The term « aryl » designates an aromatic, monocyclic or multicyclic ring with 6 to 10 carbon atoms. As examples of aryl groups, particular mention may be made of phenyl or naphtyl.

The term « arylalkyl » designates an aryl-alkyl group, in which the aryl and alkyl are such as described in the present document. As examples of arylalkyl groups, particular mention may be made of benzyl, 2-phenethyl and naphtalenemethyl.

The term « heterocyclic group » designates a carbocyclic group, substituted or non-substituted, mono- or multicyclic, in which the ring part comprises at least one heteroatom such as O, N, or S. The nitrogen or sulphur may optionally be oxidized, and the nitrogen may optionally be substituted in the aromatic rings. The heterocyclic groups comprise the heteroaryl groups and heterocycloalkyl groups.

The term « heterocycloalkyl » designates a cycloalkyl group in which one or more carbon atoms of the ring are substituted by at least one atom chosen from among O, N, or S. As examples of heterocycloalkyl groups, particular mention may be made of pyrrolidinyl, pyrrolinyl, imidazolidinyl, imidazolinyl, pirazolidinyl, pirazolinyl, pyrazalinyl, piperidyl, piperazinyl, morpholinyl, thiomorpholinyl, tetrahydrofuranyl, dithiolyl, oxathiolyl, oxadiazolyl, oxathiazolyl, pyranyl, oxazinyl, oxathiazinyl, and oxadiazinyl.

The term « heteroaryl » or « heteroaromatic » designates a group containing 5 to 10 carbon atoms in which at least one carbon of the ring is replaced by at least one atom chosen from among —O—, —N—, or —S—. As examples of heteroaryl groups particular mention may be made of pyrrolyl, furanyl, thienyl, pirazolyl, imidazolyl, thiazolyl, isothiazolyle, isoxazolyl, oxazolyl, oxathiolyl, oxadiazolyl, triazolyl, oxatriazolyl, furazanyl, tetrazolyl, pyridyl, pyrazinyl, pyrimidinyl, pyridazinyl, triazinyl, indolyl, isoindolyl, indazolyl, benzofuranyl, isobenzofuranyl, purinyl, quinazolinyl, quinolyl, isoquinolyl, benzoimidazolyl, benzothiazolyl, benzothiophenyl, thianaphthenyl, benzoxazolyl, benzisoxazolyl, cinnolinyl, phthalazinyl, naphthyridinyl, and quinoxalinyl. Also included in the definition of « heteroaryl » groups are fused ring systems, notably those including ring systems in which the aromatic ring is fused with a heterocycloalkyl ring. As examples of said fused ring systems, particular mention may be made of phthalamide, phthalic anhydride, indoline, isoindoline and tetrahydroisoquinoline.

The term « heteroarylalkyl » designates an aryl-heteroaryl group, in which the heteroaryl and the alkyl are such as described in the present document.

The terms « alkylene, cycloalkylene, heterocycloalkylene, arylene, heteroarylene » respectively designate bivalent alkyl, cycloalkyl, heterocycloalkyl aryl and heteroaryl groups, these groups being such as defined above.

FIGURES

FIG. 1: Solid-liquid transition temperature of bromide compounds of 1-alkyl-3-[4-(5-phenyl-oxazol-2-yl)-benzyl]-3H-imidazol-1-ium.

Figure 2:
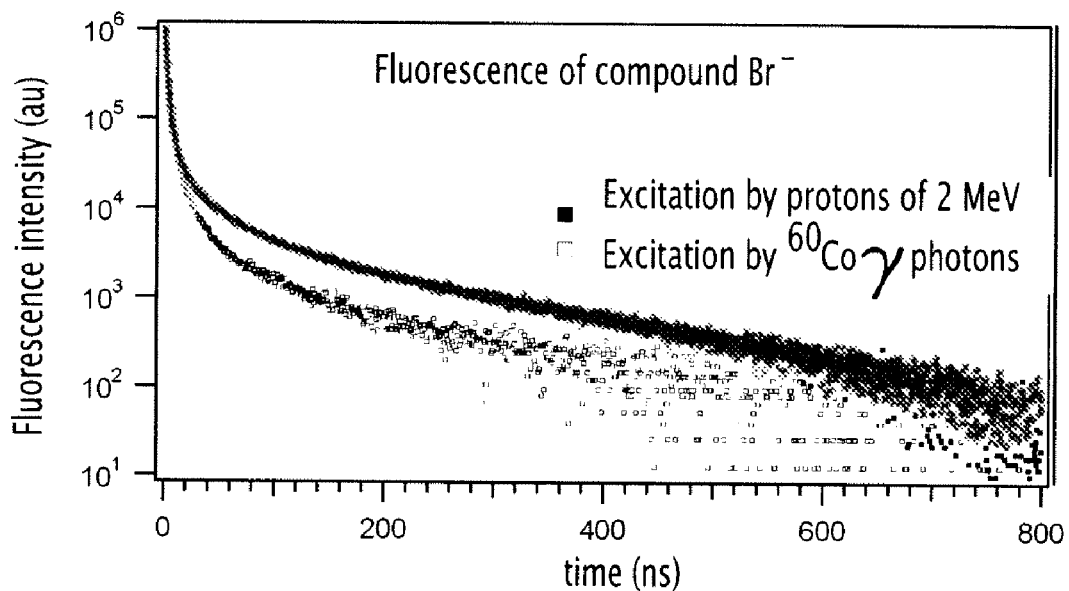
Figure 3:
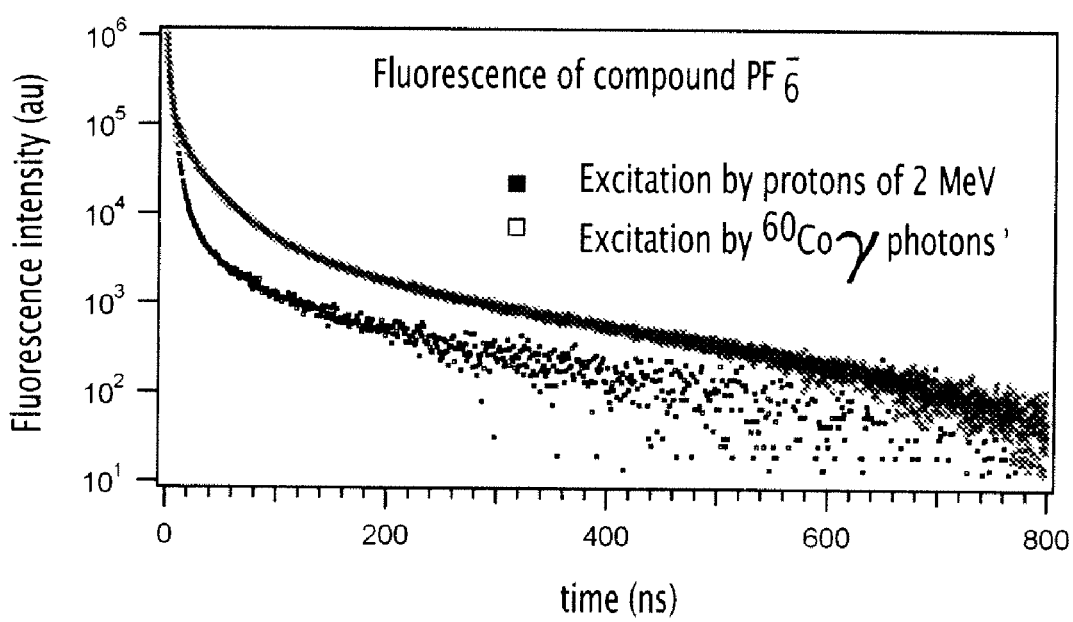
Figure 4:
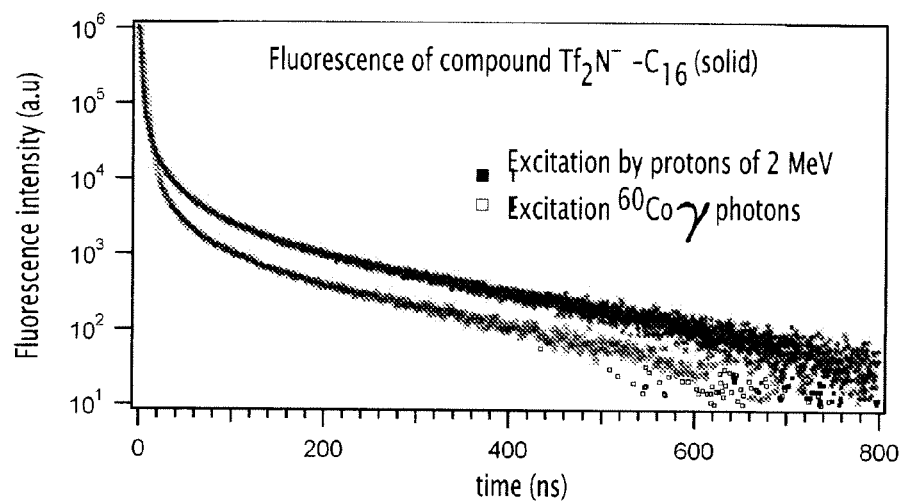

FIGS. 2 to 4: Fluorescence decay curves obtained with the $C_{16}$ compounds of Examples 7 (FIG. 2), 8 (FIG. 3) and 9 (FIG. 4) by CoC60 photons and protons of 2 MeV.

Figure 5:
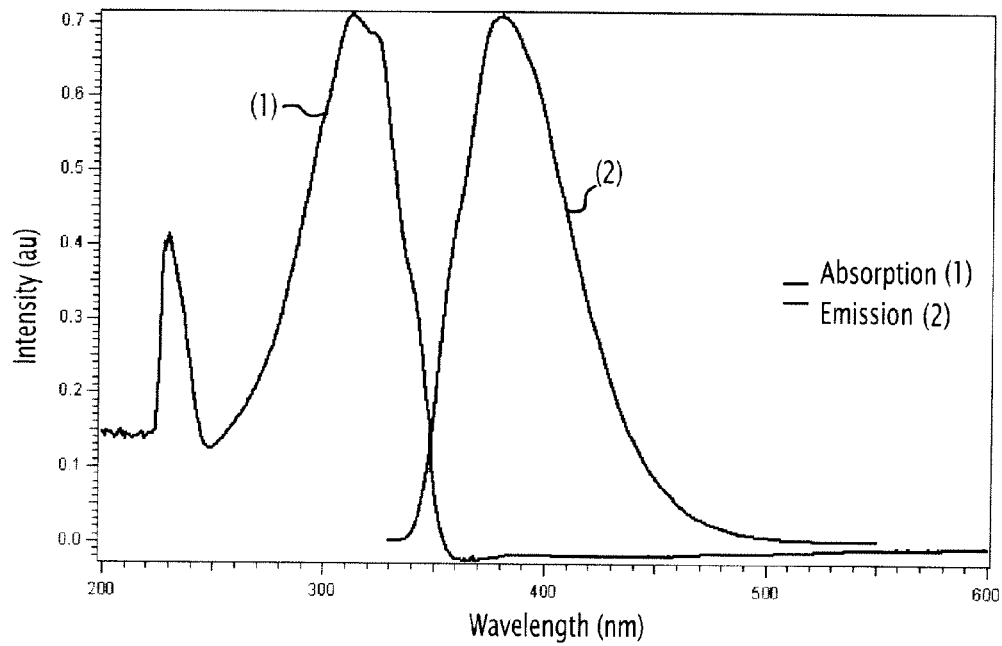

FIG. 5: Emission and absorption spectra of the $C_{16}$ compound in Example 7.

Figure 6:
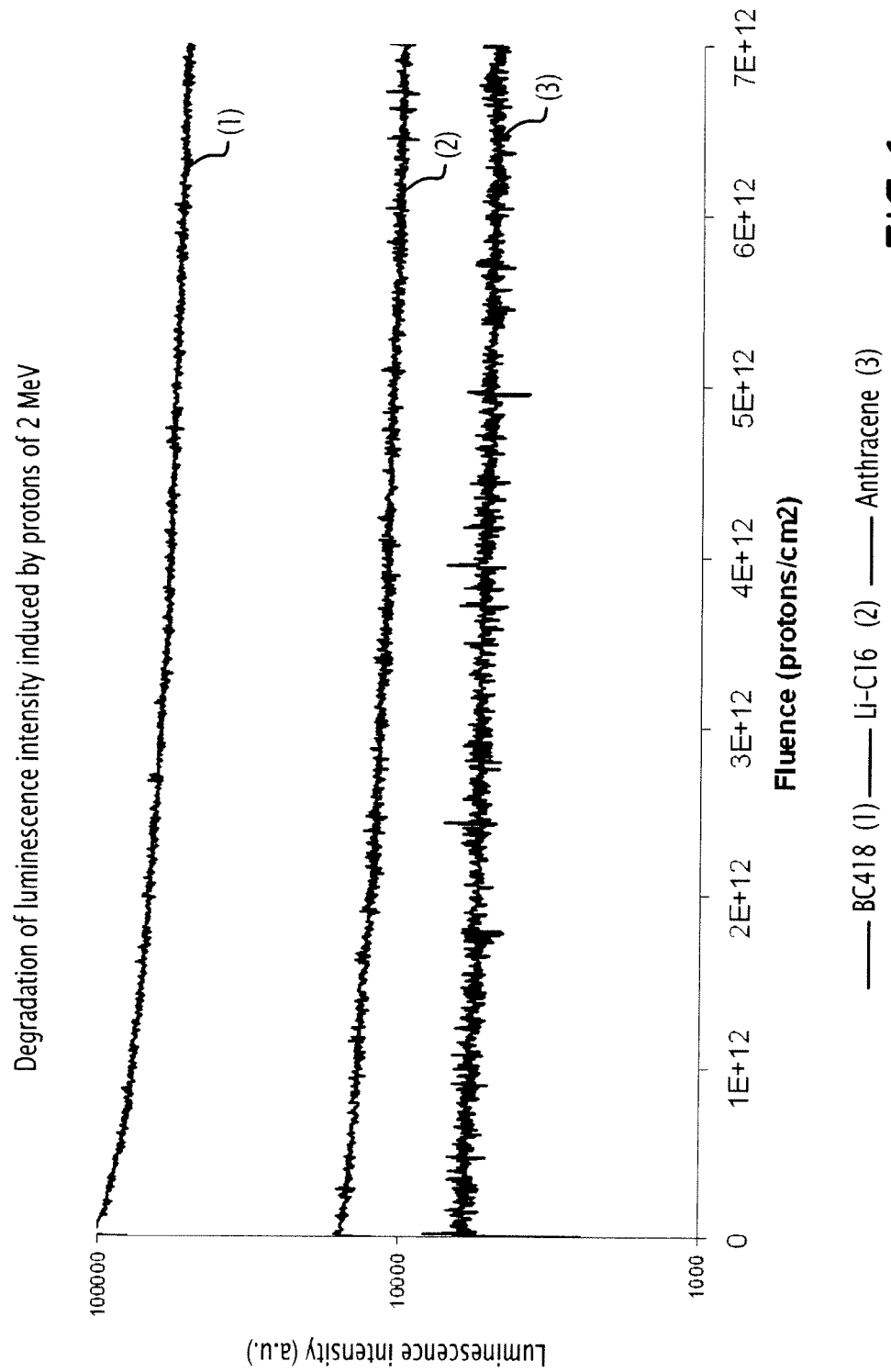

FIG. 6: Degradation of scintillation intensity for the compounds of Examples 5 and 7, anthracene and BC418, resulting from damage inflicted on the materials by protons of 2 MeV.

Figures 7, 8:
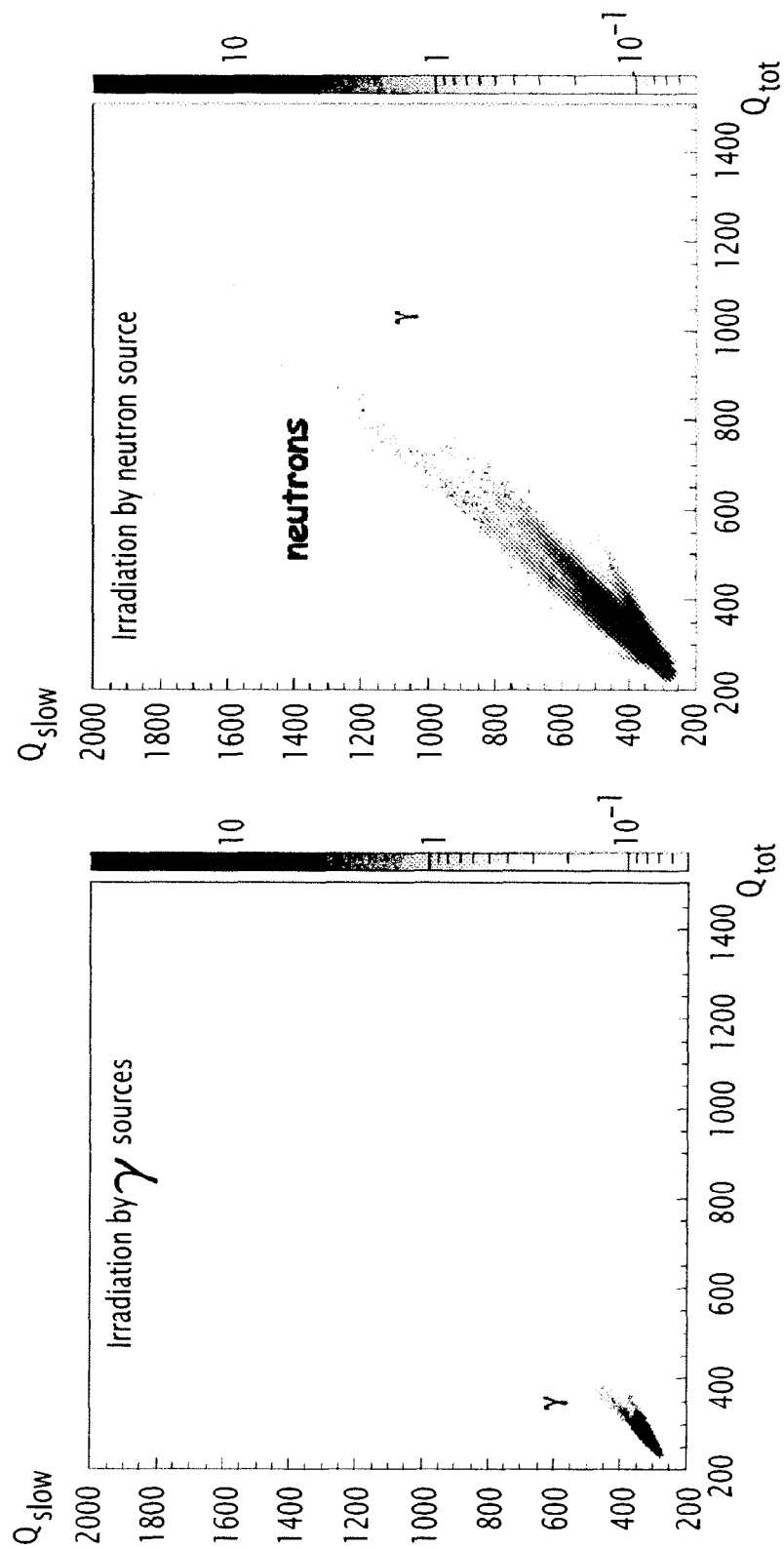

FIGS. 7-8: Neutron-gamma discriminating property of the compound in Example 9 tested using radiation sources of $^{22}$Na+$^{60}$Co (gamma radiation) and americium-beryllium (Am Be) (neutron radiation).

EXAMPLES

The following examples illustrate but do not limit the invention. The starting products used are known products, or products prepared following known operating modes.

The percentages are weight percentages unless indication is given to the contrary.

Example 1

1-Methyl-3-[4-(5-phenyl-oxazol-2-yl)-benzyl]-3H-imidazol-1-ium bromide, 1a

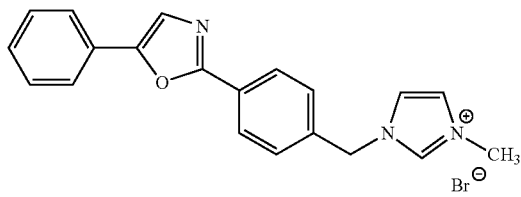 [SMILES: C[n+]1ccn(Cc2ccc(-c3ncc(-c4ccccc4)o3)cc2)c1 ; [Br-]]

To a round-bottomed flask previously purged with anhydrous argon are added 1-methylimidazole (Aldrich) (0.257 mL, 0.265 g, 3.2 mmol), 2-(4-bromomethyl-phenyl)-5-phenyl-oxazole [1] (1.013 g, 3.224 mmol) and anhydrous THF (15 mL).

The reaction mixture is stirred at 80° C. for 12 hours. During the reaction, a precipitate is formed.

A white solid is isolated by filtering, washed twice with 10 mL THF and dried under reduced pressure at ambient temperature. The product is purified by flash chromatography (silica gel column, elution DCM-MeOH, MeOH 1% to 7%) and characterized as being an imidazolium salt.

$C_{20}H_{18}BrN_3O+1.6\,H_2O=425.10$ g.mol$^{-1}$

Yield as colourless crystalline solid: (1.205 g, 94%)

$C_{20}H_{18}BrN_3O$; 1.6 H$_2$O Found (%): C, 56.57; H, 4.49; N, 10.03

Theoretical (%): C, 56.51; H, 5.03; N, 9.88

Mp=190±1° C.

NMR experiments were conducted in CDCl$_3$. ($^1$H NMR: 6 mg/0.3 mL CDCl$_3$) $^1$H NMR (300 MHz, CDCl$_3$, 20° C.): δ 10.72 ppm (s, 1 H, N—CH—N imidazolium), 8.11 (d, 2H, aromatic =CH—, $^3$J=8.5 Hz), 7.67 (m, 4H, aromatic =CH—), 7.45 (m, 3H, aromatic =CH—), 7.32 (m, 3H, aromatic =CH—), 5.72 (s, 2H, Ph-CH$_2$—N), 4.09 (s, 3H, N—CH$_3$).

$^{13}$C {$^1$H} NMR (75 MHz, CDCl$_3$, 20° C.): δ 36.83 ppm (Ph-CH$_2$—N), 52.78 (N—CH$_3$), 122.06 (aromatic C), 123.47 (aromatic C), 123.55 (aromatic C), 124.18 (aromatic C), 127.01(aromatic C), 127.56 (aromatic C), 128.27 (aromatic C), 128.62 (aromatic C), 128.91 (aromatic C), 129.50 (aromatic C), 135.02 (aromatic C), 137.51 (N—CH—N imidazolium), 151.63 (aromatic C), 159.97 (aromatic C).

IR: 3141, 3088, 3057, 2998, 2859, 1766, 1739, 1649 (s), 1561 (s), 1493 (s), 1451 (s), 1420 (s), 1334, 1283, 1169 (s), 1133, 1065, 1021, 947, 872, 831, 764, 723, 689, 613 cm$^{-1}$.

Example 2

1-Hexyl-3-[4-(5-phenyl-oxazol-2-yl)-benzyl]-3H-imidazol-1-ium bromide, 1b

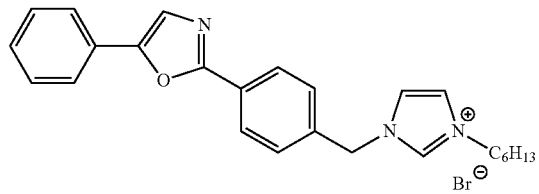

The experimental procedure is identical to the procedure for compound 1a (1-hexylimidazole [2-5] 0.787 g, 5.2 mmol, 2-(4-bromomethyl-phenyl)-5-phenyl-oxazole 1.390 g, 4.4 mmol).

$C_{25}H_{28}BrN_3O+0.5\,H_2O=475.42$ g.mol$^{-1}$

Yield as colourless crystalline solid: (1.908 g, 92%)

$C_{25}H_{28}BrN_3O$; 0.5 H$_2$O Found (%): C, 63.03; H, 6.10; N, 8.69

Theoretical (%): C, 63.16; H, 6.15; N, 8.84

Mp=150±1° C.

$^1$H NMR (300 MHz, CDCl$_3$, 20° C.): δ 10.88 ppm (s, 1H, N—CH—N imidazolium), 8.11 (d, 2H, aromatic =CH—, $^3$J=8.2 Hz), 7.67 (m, 4H, aromatic =CH—), 7.40 (m, 5H, aromatic =CH—), 7.24 (m, 1H, aromatic =CH—), 5.77 (s, 2H, Ph-CH$_2$—N), 4.30 (t, 2H, N—CH$_2$—CH$_2$—(CH$_2$)$_3$—CH$_3$, $^3$J=7.55 Hz), 1.92 (m, 2H, N—CH$_2$—CH$_2$—(CH$_2$)$_3$—CH$_3$), 1.31 (m, 6H, N—CH$_2$—CH$_2$—(CH$_2$)$_3$—CH$_3$), 0.87 (t, 3H, N—CH$_2$—CH$_2$—(CH$_2$)$_3$—CH$_3$, $^3$J=6.9 Hz).

$^{13}$C {$^1$H} NMR (75 MHz, CDCl$_3$, 20° C.): δ 13.79 (N—(CH$_2$)$_5$—CH$_3$) ppm, 22.24 (N—(CH$_2$)$_4$—CH$_2$—CH$_3$), 25.77 (N—(CH$_2$)$_3$—CH$_2$—CH$_2$—CH$_3$), 30.02 (N—(CH$_2$)$_2$—CH$_2$—(CH$_2$)$_2$—CH$_3$), 30.90 (N—CH$_2$—CH$_2$—(CH$_2$)$_3$—CH$_3$), 50.15 (N—CH$_2$—CH$_2$—(CH$_2$)$_3$—CH$_3$), 52.50 (Ph-CH$_2$—N), 122.25 (aromatic C), 122.41 (aromatic C), 123.44 (aromatic C), 124.09 (aromatic C), 126.91 (aromatic C), 127.52 (aromatic C), 128.16 (aromatic C), 128.54 (aromatic C), 128.86 (aromatic C), 129.50 (aromatic C), 135.26 (aromatic C), 136.70 (N—CH—N imidazolium), 151.53 (aromatic C), 159.96 (aromatic C).

IR: 3121, 3063, 2961, 2939, 2854, 1744, 1645, 1557 (s), 1491 (s), 1456 (s), 1418, 1358, 1324, 1154 (s), 1111, 1057, 1020, 949, 862, 838, 818, 764 (s), 716 (s), 687, 646, cm$^{-1}$.

Example 3

1-Octyl-3-[4-(5-phényl-oxazol-2-yl)-benzyl]-3H-imidazol-1-ium bromide, 1c

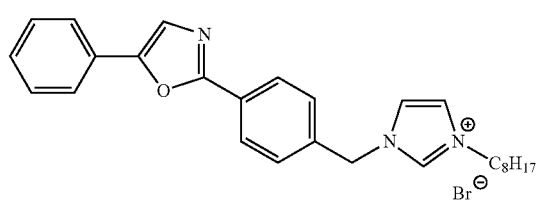

The experimental procedure is identical to the procedure for compound 1a (1-octylimidazole [2-5] 0.865 g, 4.8 mmol, 2-(4-bromomethyl-phenyl)-5-phenyl-oxazole 1.495 g, 4.8 mmol)

$C_{27}H_{32}BrN_3O+0.25\ H_2O=498.97\ g.mol^{-1}$

Yield as colourless crystalline solid: (2.134 g, 90%)

$C_{27}H_{32}BrN_3O$; 0.25 $H_2O$ Found (%): C, 64.84; H, 6.29; N, 8.22

Theoretical (%): C, 64.99; H, 6.57; N, 8.42

Mp=117±1° C.

$^1$H NMR (300 MHz, CDCl$_3$, 20° C.): δ 10.92 ppm (s, 1H, N—CH—N imidazolium), 8.11 (d, 2H, aromatic =CH—, $^3J$=8.2 Hz), 7.68 (m, 4H, aromatic =CH—), 7.45 (m, 3H, aromatic =CH—), 7.35 (m, 2H, aromatic =CH—), 7.23 (m, 1H, aromatic =CH—), 5.77 (s, 2H, Ph-CH$_2$—N), 4.29 (t, 2H, N—CH$_2$—CH$_2$—(CH$_2$)$_5$—CH$_3$, $^3J$=7.6Hz), 1.93 (m, 2H, N—CH$_2$—CH$_2$—(CH$_2$)$_5$—CH$_3$), 1.24 (m, 10H, N—CH$_2$—CH$_2$—(CH$_2$)$_5$—CH$_3$), 0.86 (t, 3H, N—CH$_2$—CH$_2$—(CH$_2$)$_5$—CH$_3$, $^3J$=6.6 Hz).

$^{13}$C {$^1$H} NMR (75 MHz, CDCl$_3$, 20° C.): δ 13.94 (N—(CH$_2$)$_7$—CH$_3$) ppm, 22.45 (N—(CH$_2$)$_6$—CH$_2$—CH$_3$), 26.18 (N—(CH$_2$)$_5$—CH$_2$—CH$_2$—CH$_3$), 28.80 (N—(CH$_2$)$_4$—CH$_2$—(CH$_2$)$_2$—CH$_3$), 28.90 (N—(CH$_2$)$_3$—CH$_2$—(CH$_2$)$_3$—CH$_3$), 30.11 (N—(CH$_2$)$_2$—CH$_2$—(CH$_2$)$_4$—CH$_3$), 31.53 (N—CH$_2$—CH$_2$—(CH$_2$)$_5$—CH$_3$), 50.22 (N—CH$_2$—CH$_2$—(CH$_2$)$_5$-CH$_3$), 52.59(Ph-CH$_2$—N), 122.11 (aromatic C), 122.33 (aromatic C), 123.47, 124.13 (aromatic C), 126.96 (aromatic C), 127.57 (aromatic C), 128.23 (aromatic C), 128.56 (aromatic C), 128.88 (aromatic C), 129.52 (aromatic C), 135.21 (aromatic C), 136.85 (N—CH—N imidazolium), 151.58 (aromatic C), 159.98 (aromatic C).

IR: 3065, 2926, 2854, 1648, 1559 (s), 1489, 1454 (s), 1420, 1360, 1157 (s), 1117, 1020, 949, 860, 771, 719, 689 cm$^{-1}$.

Example 4

1-Decyl-3-[4-(5-phenyl-oxazol-2-yl)-benzyl]-3H-imidazol-1-ium bromide, 1d

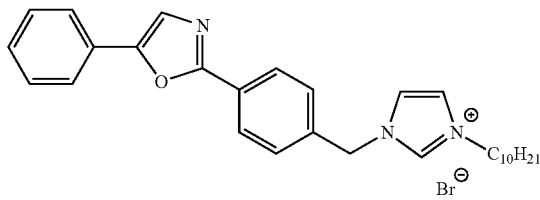

The experimental procedure is identical to the procedure for compound 1a (1-decylimidazole [2-5] 0.973 g, 4.7 mmol, 2-(4 bromomethyl-phenyl)-5-phenyl-oxazole 1.383 g, 4.4 mmol)

$C_{29}H_{36}BrN_3O+0.5\ H_2O=531.53\ g.mol^{-1}$

Yield as colourless crystalline solid: (2.111 g, 92%)

$C_{29}H_{36}BrN_3O$; 0.5 $H_2O$ Found (%): C, 65.61; H, 7.09; N, 7.85

Theoretical (%): C, 65.53; H, 7.02; N, 7.91

Mp=136±1° C.

$^1$H NMR (300 MHz, CDCl$_3$, 20° C.): δ 10.93 ppm (s, 1H, N—CH—N imidazolium), 8.12 (d, 2H, aromatic =CH—, $^3J$=8.2 Hz), 7.68 (m, 4H, aromatic =CH—), 7.34 (m, 6H, aromatic =CH—), 5.77 (s, 2H, Ph-CH$_2$—N), 4.30 (t, 2H, N—CH$_2$—CH$_2$—(CH$_2$)$_7$—CH$_3$, $^3J$=7.5 Hz), 1.93 (m, 2H, N—CH$_2$—CH$_2$—(CH$_2$)$_7$—CH$_3$), 1.24 (m, 14H, N—CH$_2$—CH$_2$—(CH$_2$)$_7$—CH$_3$), 0.87(t, 3H, N—CH$_2$—CH$_2$—(CH$_2$)$_7$—CH$_3$, $^3J$=6.6 Hz).

$^{13}$C {$^1$H} NMR (75 MHz, CDCl$_3$, 20° C.): δ 13.98 (N—(CH$_2$)$_9$—CH$_3$) ppm, 22.52 (N—(CH$_2$)$_8$—CH$_2$—CH$_3$), 26.17 (N—(CH$_2$)$_7$—CH$_2$—CH$_2$—CH$_3$), 28.84 (N—(CH$_2$)$_6$—CH$_2$—(CH$_2$)$_2$—CH$_3$), 29.10 (N—(CH$_2$)$_5$—CH$_2$—(CH$_2$)$_3$—CH$_3$), 29.24 (N—(CH$_2$)$_4$—CH$_2$—(CH$_2$)$_4$—CH$_3$), 29.30 (N—(CH$_2$)$_3$—CH$_2$—(CH$_2$)$_5$—CH$_3$), 30.11 (N—(CH$_2$)$_2$—CH$_2$—(CH$_2$)$_6$—CH$_3$), 31.70 (N—CH$_2$—CH$_2$—(CH$_2$)$_7$—CH$_3$), 50.18 (N—CH$_2$—CH$_2$—(CH$_2$)$_7$—CH$_3$), 52.53 (Ph-CH$_2$—N), 122.19 (aromatic C), 122.42 (aromatic C), 123.44 (aromatic C), 124.09 (aromatic C), 126.91 (aromatic C), 127.54 (aromatic C), 128.19 (aromatic C), 128.54 (aromatic C), 128.85 (aromatic C), 129.51 (aromatic C), 135.25 (aromatic C), 136.73 (N—CH—N imidazolium), 151.53 (aromatic C), 159.96 (aromatic C).

IR: 3078, 2992, 2922, 2851, 1749, 1645, 1558 (s), 1488, 1445, 1365, 1331, 1160 (s), 1118, 1059, 949, 876, 821, 767, 720, 691, 655 cm$^{-1}$.

Example 5

1-Dodecyl-3-[4-(5-phenyl-oxazol-2-yl)-benzyl]-3H-imidazol-1-ium bromide, 1e

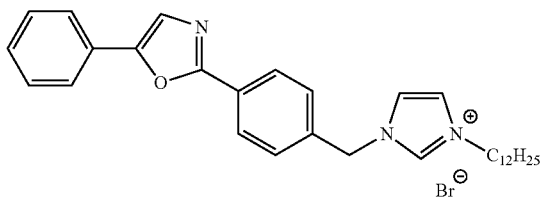

The experimental procedure is identical to the procedure for compound 1a (1-dodecylimidazole [2-5] 1.262 g, 5.3 mmol, 2-(4-bromomethyl-phenyl)-5-phenyl-oxazole 1.342 g, 4.3 mmol)

$C_{31}H_{40}BrN_3O+0.15\ H_2O=553.28\ g.mol^{-1}$

Yield as colourless crystalline solid: (2.23 g, 95%)

$C_{31}H_{40}BrN_3O$; 0.15 $H_2O$ Found (%): C, 67.25; H, 7.28; N, 7.40

Theoretical (%): C, 67.30; H, 7.34; N, 7.59

Mp=152±1° C.

$^1$H NMR (300 MHz, CDCl$_3$, 20° C.): δ 10.96 ppm (s, 1H, N—CH—N imidazolium), 8.12 (d, 2H, aromatic =CH—, $^3J$=8.5 Hz), 7.68 (m, 4H, aromatic =CH—), 7.45 (m, 3H, aromatic =CH—), 7.36 (m, 1H, aromatic =CH—), 7.30 (m, 1H, aromatic =CH—), 7.22 (m, 1H, aromatic =CH—), 5.77 (s, 2H, Ph-CH$_2$—N), 4.29 (t, 2H, N—CH$_2$—(CH$_2$)$_{10}$—CH$_3$, $^3J$=7.5 Hz), 1.93 (m, 2H, N—CH$_2$—CH$_2$—(CH$_2$)$_9$—CH$_3$), 1.24 (m, 18H, N—CH$_2$—CH$_2$—(CH$_2$)$_9$—CH$_3$), 0.87 (t, 3H, N—CH$_2$—(CH$_2$)$_{10}$—CH$_3$, $^3J$=6.72 Hz).

$^{13}$C {$^1$H} NMR (75 MHz, CDCl$_3$, 20° C.): δ 14.03 (N—(CH$_2$)$_{11}$—CH$_3$) ppm, 22.58 (N—(CH$_2$)$_{10}$—CH$_2$—CH$_3$), 26.20 (N—(CH$_2$)$_9$—CH$_2$—CH$_2$—CH$_3$), 28.88 (N—(CH$_2$)$_8$—CH$_2$—(CH$_2$)$_2$—CH$_3$), 29.22 (N—(CH$_2$)$_7$—CH$_2$—(CH$_2$)$_3$—CH$_3$), 29.29 (N—(CH$_2$)$_6$—CH$_2$—(CH$_2$)$_4$—CH$_3$), 29.40 (N—(CH$_2$)$_5$—CH$_2$—(CH$_2$)$_5$—CH$_3$), 29.49 (N—(CH$_2$)$_3$—(CH$_2$)$_2$—(CH$_2$)$_6$—CH$_3$), 30.13 (N—(CH$_2$)$_2$—CH$_2$—(CH$_2$)$_8$—CH$_3$), 31.79 (N—CH$_2$—CH$_2$—(CH$_2$)$_9$—CH$_3$), 50.23 (N—CH$_2$—(CH$_2$)$_{10}$—CH$_3$), 52.61 (Ph-CH$_2$—N), 122.06 (aromatic C), 122.30 (aromatic C), 123.47 (aromatic C), 124.13

(aromatic C), 126.96 (aromatic C), 127.57 (aromatic C), 128.24 (aromatic C), 128.58 (aromatic C), 128.89 (aromatic C), 129.54 (aromatic C), 135.18 (aromatic C), 136.89 (N—CH—N imidazolium), 151.58 (aromatic C), 159.98 (aromatic C).

IR: 3082, 3015, 2919, 2848, 1735, 1560, 1489, 1443, 1364, 1159 (s), 1056, 949, 874, 812, 764, 719, 691, 654 cm$^{-1}$.

Example 6

3-[4-(5-Phényl-oxazol-2-yl)-benzyl]-1-tétradécyl-3H-imidazol-1-ium bromide, 1f

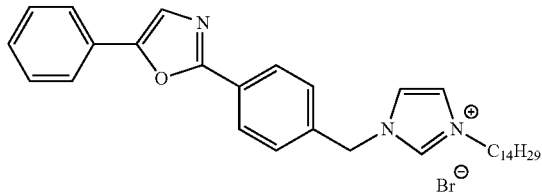

To a round-bottomed flask previously purged with anhydrous argon are added 1-tetradecylimidazole [2-5] (1.023 g, 3.9 mmol), 2-(4-bromomethyl-phenyl)-5-phenyl-oxazole (1.215 g, 3.9 mmol) and anhydrous THF (15 mL). The reaction mixture is stirred at 80° C. for 12 hours. The solvent is removed in vacuo and the product is washed with 3 times 10 mL Et$_2$O and dried under reduced pressure at ambient temperature. The product is purified by flash chromatography (silica gel column, elution with DCM-MeOH, MeOH 1% to 7%) and characterized as being an imidazolium salt.

$C_{33}H_{44}BrN_3O$=578.63 g.mol$^{-1}$
Yield as colourless crystalline solid (2.092 g, 93%)
$C_{33}H_{44}BrN_3O$ Found (%): C, 68.49; H, 7.78; N, 7.08
Theoretical (%): C, 68.50; H, 7.66; N, 7.20
Mp=117±1° C.

$^1$H NMR (300 MHz, CDCl$_3$, 20° C.): δ 11.00 ppm (s, 1H, N—CH—N imidazolium), 8.13 (d, 2H, aromatic =CH—, $^3$J=8.2 Hz), 7.68 (m, 4H, aromatic =CH—), 7.46 (m, 3H, aromatic =CH—), 7.36 (m, 1H, aromatic =CH—), 7.26 (m, 1H, aromatic =CH—), 7.20 (m, 1H, aromatic =CH—), 5.77 (s, 2H, Ph-CH$_2$—N), 4.30 (t, 2H, N—CH$_2$—(CH$_2$)$_{12}$—CH$_3$, $^3$J=7.5 Hz), 1.94 (m, 2H, N—CH$_2$—CH$_2$—(CH$_2$)$_{11}$—CH$_3$), 1.24 (m, 22H, N—CH$_2$—CH$_2$—(CH$_2$)$_{11}$—CH$_3$), 0.87 (t, 3H, N—(CH$_2$)$_{13}$—CH$_3$, $^3$J=6.7 Hz).

$^{13}$C {$^1$H} NMR (75 MHz, CDCl$_3$, 20° C.): δ 14.03 (N—(CH$_2$)$_{13}$—CH$_3$) ppm, 22.58 (N—(CH$_2$)$_{12}$—CH$_2$—CH$_3$), 26.20 (N—(CH$_2$)$_{11}$—CH$_2$—CH$_2$—CH$_3$), 28.89 (N—(CH$_2$)$_{10}$—CH$_2$—(CH$_2$)$_2$—CH$_3$), 29.25 (N—(CH$_2$)$_9$—CH$_2$—(CH$_2$)$_3$—CH$_3$), 29.30 (N—(CH$_2$)$_8$—CH$_2$—(CH$_2$)$_4$—CH$_3$), 29.40 (N—(CH$_2$)$_7$—CH$_2$—(CH$_2$)$_5$—CH$_3$), 29.50 (N—(CH$_2$)$_5$—(CH$_2$)$_2$—(CH$_2$)$_6$—CH$_3$), 29.54 (N—(CH$_2$)$_4$—(CH$_2$)—(CH$_2$)$_8$—CH$_3$), 29.58 (N—(CH$_2$)$_3$—CH$_2$—(CH$_2$)$_9$—CH$_3$), 30.13 (N—(CH$_2$)$_2$—CH$_2$—(CH$_2$)$_{10}$—CH$_3$), 31.81 (N—CH$_2$—CH$_2$—(CH$_2$)$_{11}$—CH$_3$), 50.23 (N—CH$_2$—(CH$_2$)$_{12}$—CH$_3$), 52.61 (Ph-CH$_2$—N), 122.07 (aromatic C), 122.32 (aromatic C), 123.47 (aromatic C), 124.12 (aromatic C), 126.96 (aromatic C), 127.57 (aromatic C), 128.24 (aromatic C), 128.56 (aromatic C), 128.88 (aromatic C), 129.54 (aromatic C), 135.20 (aromatic C), 136.86 (N—CH—N imidazolium), 151.58 (aromatic C), 159.98 (aromatic C).

IR: 3127, 3096, 2917 (s), 2849 (s), 1609, 1589, 1556, 1470, 1440, 1363, 1330, 1186, 1160 (s), 1117, 1054, 951, 847, 818, 772, 717, 694, 661 cm$^{-1}$.

Example 7

1-Hexadecyl-3-[4-(5-phenyl-oxazol-2-yl)-benzyl]-3H-imidazol-1-ium bromide, 1g

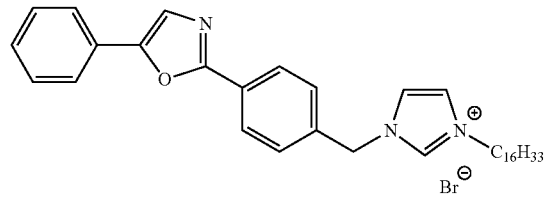

The experimental procedure is identical to the procedure for compound 1f (1-hexadecylimidazole [2-5] 1.385 g, 4.7 mmol, 2-(4-bromomethyl-phenyl)-5-phenyl-oxazole 1.489 g, 4.7 mmol)

$C_{35}H_{45}BrN_3O$=606.68 g.mol$^{-1}$
Yield as colourless crystalline solid: (2.680 g, 93%)
$C_{35}H_{45}BrN_3O$ Found (%): C, 68.86; H, 8.39; N, 7.17
Theoretical (%): C, 69.29; H, 7.97; N, 6.93
Mp=97±1° C.

$^1$H NMR (300 MHz, CDCl$_3$, 20° C.): δ 10.93 ppm (s, 1H, N—CH—N imidazolium), 8.12 (d, 2H, aromatic =CH—, $^3$J=8.5 Hz), 7.68 (m, 4H, aromatic =CH—), 7.40 (m, 4H, aromatic =CH—), 7.25 (m, 2H, aromatic =CH—), 5.77 (s, 2H, Ph-CH$_2$—N), 4.30 (t, 3H, N—CH$_2$—(CH$_2$)$_{14}$—CH$_3$, $^3$J=7.5 Hz), 1.93 (m, 2H, N—CH$_2$—CH$_2$—(CH$_2$)$_{13}$—CH$_3$), 1.23 (m, 26H, N—CH$_2$—CH$_2$—(CH$_2$)$_{13}$—CH$_3$), 0.88 (t, 3H, N—(CH$_2$)$_{15}$—CH$_3$, $^3$J=6.7 Hz).

$^{13}$C{$^1$H} NMR (75 MHz, CDCl$_3$, 20° C.): δ 14.06 (N—(CH$_2$)$_{15}$—CH$_3$) ppm, 22.63 (N—(CH$_2$)$_{14}$—CH$_2$—CH$_3$), 26.24 (N—(CH$_2$)$_{13}$—CH$_2$—CH$_2$—CH$_3$), 28.90 (N—(CH$_2$)$_{12}$—CH$_2$—(CH$_2$)$_2$—CH$_3$), 29.30 (N—(CH$_2$)$_3$—(CH$_2$)$_9$—(CH$_2$)$_3$—CH$_3$), 29.43 (N—(CH$_2$)$_3$—(CH$_2$)$_9$—(CH$_2$)$_3$—CH$_3$), 29.53 (N—(CH$_2$)$_3$—(CH$_2$)$_9$—(CH$_2$)$_3$—CH$_3$), 29.59 (N—(CH$_2$)$_3$—(CH$_2$)$_9$—(CH$_2$)$_3$—CH$_3$), 29.62 (N—(CH$_2$)$_3$—(CH$_2$)$_9$—(CH$_2$)$_3$—CH$_3$), 30.13 (N—(CH$_2$)$_2$—CH$_2$—(CH$_2$)$_{12}$—CH$_3$), 31.86 (N—CH$_2$—CH$_2$—(CH$_2$)$_{13}$—CH$_3$), 50.32 (N—CH$_2$—CH$_2$—(CH$_2$)$_{13}$—CH$_3$), 52.78 (Ph-CH$_2$—N), 121.75 (aromatic C), 121.95 (aromatic C), 123.52 (aromatic C), 124.19 (aromatic C), 127.06 (aromatic C), 127.62 (aromatic C), 128.39 (aromatic C), 128.62 (aromatic C), 128.93 (aromatic C), 129.57 (aromatic C), 134.99 (aromatic C), 137.31 (N—CH—N imidazolium), 151.66 (aromatic C), 160.00 (aromatic C).

IR: 3128, 3097, 2917 (s), 2850 (s), 1611, 1557, 1470, 1444, 1363, 1331, 1159 (s), 1122, 1058, 951, 846, 770, 720, 661 cm$^{-1}$.

Example 8

1-Hexadecyl-3-[4-(5-ph enyl-oxazol-2-yl)-benzyl]-3H-imidazol-1-ium hexafluorophosphate, 2a

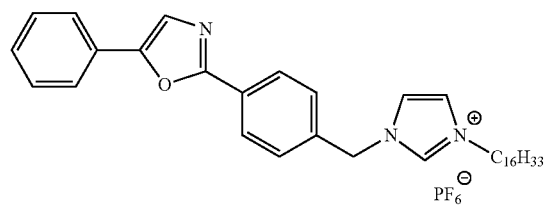

To a round-bottomed flask are added 1-hexadecyl-3-[4-(5-phenyl-oxazol-2-yl)-benzyl]-3H-imidazol-1-ium bromide (1.008 g, 1.7 mmol) dissolved in ethanol (50 mL). An aqueous solution of potassium hexafluorophosphate is added (0.490 g, 2.7 mmol, 10 mL). The mixture is stirred at ambient temperature for 3 days. The precipitate is filtered, washed 3 times with 30 mL distilled water and dried under reduced pressure at ambient temperature for 12 hours. The product is characterized by NMR spectroscopy.

$C_{35}H_{48}F_6N_3OP = 671.74$ g.mol$^{-1}$

Yield as colourless crystalline solid: (0.994 g, 89%)

Mp=114±1° C.

$^1$H NMR (300 MHz, CDCl$_3$, 20° C.): δ 8.80 ppm (s, 1H, N—CH—N imidazolium), 8.12 (d, 2H, aromatic =CH—, $^3$J=8.5 Hz), 7.70 (d, 2H, aromatic =CH—, $^3$J=7.1 Hz), 7.47 (m, 5H, aromatic =CH—), 7.35 (m, 1H, aromatic =CH—), 7.21 (m, 2H, aromatic =CH—), 5.38 (s, 2H, Ph-CH$_2$—N), 4.18 (t, 3H, N—CH$_2$—(CH$_2$)$_{14}$—CH$_3$, $^3$J=7.5 Hz), 1.89 (m, 2H, N—CH$_2$—CH$_2$—(CH$_2$)$_{13}$—CH$_3$), 1.23 (m, 26H, N—CH$_2$—CH$_2$—(CH$_2$)$_{13}$—CH$_3$), 0.88 (t, 3H, N—(CH$_2$)$_{15}$—CH$_3$, $^3$J=6.7 Hz).

$^{13}$C {$^1$H} NMR (75 MHz, CDCl$_3$, 20° C.): δ 14.05 (N—(CH$_2$)$_{15}$—CH$_3$) ppm, 22.62 (N—(CH$_2$)$_{14}$—CH$_2$—CH$_3$), 26.16 (N—(CH$_2$)$_{13}$—CH$_2$—CH$_2$—CH$_3$), 28.86 (N—(CH$_2$)$_{12}$—CH$_2$—(CH$_2$)$_2$—CH$_3$), 29.30 (N—(CH$_2$)$_2$—(CH$_2$)$_{10}$—(CH$_2$)$_3$—CH$_3$), 29.46 (N—(CH$_2$)$_2$—(CH$_2$)$_{10}$—(CH$_2$)$_3$—CH$_3$), 29.56 (N—(CH$_2$)$_2$—(CH$_2$)$_{10}$—(CH$_2$)$_3$—CH$_3$), 29.64 (N—(CH$_2$)$_2$—(CH$_2$)$_{10}$—(CH$_2$)$_3$—CH$_3$), 29.75 (N—(CH$_2$)$_2$—(CH$_2$)$_{10}$—(CH$_2$)$_3$—CH$_3$), 31.86 (N—CH$_2$—CH$_2$—(CH$_2$)$_{13}$CH$_3$), 50.31 (N—CH$_2$—CH$_2$—(CH$_2$)$_{14}$CH$_3$), 52.99 (Ph-CH$_2$—N), 122.16 (aromatic C), 122.32 (aromatic C), 123.47 (aromatic C), 124.16 (aromatic C), 127.08 (aromatic C), 127.58 (aromatic C), 128.39 (aromatic C), 128.60 (aromatic C), 128.90 (aromatic C), 129.31 (aromatic C), 134.44 (aromatic C), 135.50 (N—CH—N imidazolium), 151.65 (aromatic C), 159.90 (aromatic C).

IR: 3165, 2922, 2851, 1561, 1468, 1417, 1384, 1163, 1116, 1057, 1023, 949, 840, 818, 770, 741, 720, 693, 654 cm$^{-1}$.

Example 9

1-Hexadecyl-3-[4-(5-phényl-oxazol-2-yl)-benzyl]-3H-imidazol-1-ium bis(trifluoromethylsulphonyl)imide, 2b

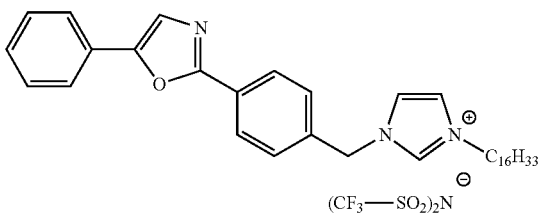

To a round-bottomed flask are added 1-hexadecyl-3-[4-(5-phenyl-oxazol-2-yl)-benzyl]-3H-imidazol-1-ium bromide (1.007 g, 1.7 mmol) which is then dissolved in ethanol (55 mL). Lithium bis(trifluoromethylsulphonyl)imide (0.731 g, 2.5 mmol) is then added. The solution is stirred at ambient temperature for 3 days. The solvent is removed under reduced pressure. The solid is washed 3 times with 30 mL distilled water and dried under reduced pressure at ambient temperature for 12 hours. The product is characterized by NMR spectroscopy.

$C_{37}H_{48}F_6N_4O_5S_2 = 806.92$ g.mol$^{-1}$

Yield as colourless crystalline solid: (1.261 g, 94%)

Mp=78±1° C.

$^1$H NMR (300 MHz, CDCl$_3$, 20° C.): δ 9.08 ppm (s, 1H, N—CH—N imidazolium), 8.16 (d, 2H, aromatic =CH—, $^3$J=8.2 Hz), 7.72 (d, 2H, aromatic =CH—, $^3$J=7.1 Hz), 7.48 (m, 5H, aromatic =CH—), 7.37 (m, 1H, aromatic =CH—), 7.23 (d, 2H, aromatic =CH—, $^3$J=7.1 Hz), 5.44 (s, 2H, Ph-CH$_2$—N), 4.22 (t, 2H, N—CH$_2$—(CH$_2$)$_{14}$—CH$_3$, $^3$J=7.5 Hz), 1.89 (m, 2H, N—CH$_2$—CH$_2$—(CH$_2$)$_{13}$—CH$_3$), 1.24 (m, 26H, N—CH$_2$—CH$_2$—(CH$_2$)$_{13}$—CH$_3$), 0.88 (t, 3H, N—(CH$_2$)$_{15}$—CH$_3$, $^3$J=6.7 Hz).

$^{13}$C {$^1$H} NMR (75 MHz, CDCl$_3$, 20° C.): δ 14.05 (N—(CH$_2$)$_{15}$—CH$_3$) ppm, 22.63 (N—(CH$_2$)$_{14}$—CH$_2$—CH$_3$), 26.07 (N—(CH$_2$)$_{13}$—CH$_2$—CH$_2$—CH$_3$), 28.79 (N—(CH$_2$)$_{12}$—CH$_2$—(CH$_2$)$_2$—CH$_3$), 29.25 (N—(CH$_2$)$_2$—(CH$_2$)$_{10}$—(CH$_2$)$_3$—CH$_3$), 29.30 (N—(CH$_2$)$_2$—(CH$_2$)$_{10}$—(CH$_2$)$_3$—CH$_3$), 29.41 (N—(CH$_2$)$_2$—(CH$_2$)$_{10}$—(CH$_2$)$_3$—CH$_3$), 29.53 (N—(CH$_2$)$_2$—(CH$_2$)$_{10}$—(CH$_2$)$_3$—CH$_3$), 29.59 (N—(CH$_2$)$_2$—(CH$_2$)$_{10}$—(CH$_2$)$_3$—CH$_3$), 29.63 (N—(CH$_2$)$_2$—(CH$_2$)$_{10}$—(CH$_2$)$_3$—CH$_3$), 29.97 (N—(CH$_2$)$_2$—(CH$_2$)$_{10}$—(CH$_2$)$_3$—CH$_3$), 31.86 (N—CH$_2$—CH$_2$—(CH$_2$)$_{13}$.CH$_3$), 50.34 (N—CH$_2$—CH$_2$—(CH$_2$)$_{14}$.CH$_3$), 53.06 (Ph-CH$_2$—N) 119.80 (q, CF$_3$—, J=321.1 Hz), 122.37 (aromatic C), 122.54 (aromatic C), 123.49 (aromatic C), 124.19 (aromatic C), 127.15 (aromatic C), 127.58 (aromatic C), 128.55 (aromatic C), 128.67 (aromatic C), 128.93 (aromatic C), 129.26 (aromatic C), 134.36 (aromatic C), 135.46 (N—CH—N imidazolium), 151.74 (aromatic C), 159.94 (aromatic C).

IR: 3141, 3084, 2919, 2851, 1937, 1849, 1800, 1590, 1560, 1493, 1466, 1416, 1351, 1181, 1138, 1059, 952, 906, 848, 824, 790, 764, 718, 687, 655, 615 cm$^{-1}$.

Example 10

1-Hexadecyl-3-[4-(5-phenyl-oxazol-2-yl)-benzyl]-3H-imidazol-1-ium dodecyl sulphate, 2c

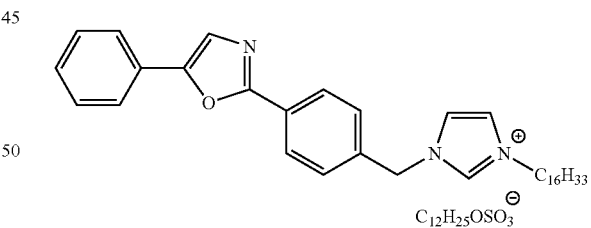

To a round-bottomed flask is added 1-hexadecyl-3-[4-(5-phenyl-oxazol-2-yl)-benzyl]-3H-imidazol-1-ium bromide (1.005 g, 1.7 mmol) which is then dissolved in methanol (100 mL). Sodium dodecyl sulphate (0.783 g, 2.7 mmol, 50 mL MeOH) is added. The mixture is stirred at ambient temperature for 12 hours.

The white solid is isolated by filtration, washed 3 times with 30 mL water and dried under reduced pressure at ambient temperature for 12 hours. The product is characterized by NMR spectroscopy.

$C_{47}H_{73}N_3O_5S = 792.16$ g.mol$^{-1}$

Yield as colourless crystalline solid: (1.053 g, 80%)

Mp=127±1° C.

$^1$H NMR (300 MHz, CDCl$_3$, 20° C.): δ 10.04 ppm (s, 1H, N—CH—N imidazolium), 8.13 (d, 2H, aromatic =CH—, $^3$J=8.2 Hz), 7.71 (d, 2H, aromatic =CH—, $^3$J=7.1 Hz), 7.59 (d, 2H, aromatic =CH—, $^3$J=8.2 Hz), 7.45 (m, 3H, aromatic =CH—), 7.36 (m, 1H, aromatic =CH—), 7.19 (m, 2H, =aromatic CH—), 5.57 (s, 2H, Ph-CH$_2$—N), 4.25 (t, 2H, N—CH$_2$—(CH$_2$)$_{14}$—CH$_3$, $^3$J=7.5 Hz), 4.10 (t, 2H, CH$_3$—(CH$_2$)$_9$—CH$_2$—CH$_2$—OSO$_3^-$, $^3$J=6.8 Hz), 1.90 (m, 2H, N—CH$_2$—CH$_2$—(CH$_2$)$_{13}$—CH$_3$), 1.68 (m, 2H, CH$_3$—(CH$_2$)$_9$—CH$_2$—CH$_2$—OSO$_3$), 1.24 (m, 44H, N—CH$_2$—CH$_2$—(CH$_2$)$_{13}$—CH$_3$) and CH$_3$—(CH$_2$)$_9$—CH$_2$—CH$_2$—OSO$_3^-$), 0.87 (m, 6H, N—(CH$_2$)$_{15}$—CH$_3$ and CH$_3$—(CH$_2$)$_9$—CH$_2$—CH$_2$—OSO$_3^-$, $^3$J=6.7 Hz).
$^{13}$C {$^1$H} NMR (75 MHz, CDCl$_3$, 20° C.): δ 14.03 (N—(CH$_2$)$_{15}$—CH$_3$) and C$_3$—(CH$_2$)$_{11}$—OSO$_3^-$) ppm, 22.60 (N—(CH$_2$)$_{14}$—CH$_2$—CH$_3$) and CH$_3$—CH$_2$-(CH$_2$)$_{10}$—OSO$_3^-$), 25.92 (N—(CH$_2$)$_{13}$—CH$_2$—CH$_2$—CH$_3$) and CH$_3$—CH$_2$—CH$_2$—(CH$_2$)$_9$—OSO$_3^-$), 26.24 (N—(CH$_2$)$_{12}$—CH$_2$—(CH$_2$)$_2$—CH$_3$) and CH$_3$—(CH$_2$)$_2$—CH$_2$—(CH$_2$)$_8$—OSO$_3^-$), 28.94 (N—(CH$_2$)$_2$—(CH$_2$)$_{10}$—(CH$_2$)$_3$—CH$_3$) and CH$_3$—(CH$_2$)$_3$—(CH$_2$)$_6$—(CH$_2$)$_2$—OSO$_3^-$), 29.29 (N—(CH$_2$)$_2$—(CH$_2$)$_{10}$—(CH$_2$)$_3$—CH$_3$) and CH$_3$—(CH$_2$)$_3$—(CH$_2$)$_6$—(CH$_2$)$_2$—OSO$_3^-$), 29.36 (N—(CH$_2$)$_2$—(CH$_2$)$_{10}$—(CH$_2$)$_3$—CH$_3$) and CH$_3$—(CH$_2$)$_3$—(CH$_2$)$_6$—(CH$_2$)$_2$—OSO$_3$), 29.42 (N—(CH$_2$)$_2$—(CH$_2$)$_{10}$—(CH$_2$)$_3$—CH$_3$) and CH$_3$—(CH$_2$)$_3$—(CH$_2$)$_6$—(CH$_2$)$_2$—OSO$_3^-$), 29.48 (N—(CH$_2$)$_2$—(CH$_2$)$_{10}$—(CH$_2$)$_3$—CH$_3$) and CH$_3$—(CH$_2$)$_3$—(CH$_2$)$_6$—(CH$_2$)$_2$—OSO$_3$), 29.59 (N—(CH$_2$)$_2$—(CH$_2$)$_{10}$—(CH$_2$)$_3$—CH$_3$) and CH$_3$—(CH$_2$)$_3$—(CH$_2$)$_6$—(CH$_2$)$_2$—OSO$_3$), 30.06 (CH$_3$—(CH$_2$)$_9$—CH$_2$—CH$_2$—OSO$_3^-$), 31.85 (N—CH$_2$—CH$_2$—(CH$_2$)$_{13}$-CH$_3$), 50.15 (CH$_3$—(CH$_2$)$_9$—CH$_2$—CH$_2$—OSO$_3^-$), 52.74 (N—CH$_2$—CH$_2$—(CH$_2$)$_{14}$-CH$_3$), 67.73 (Ph-CH$_2$—N), 122.03 (aromatic C), 122.24 (aromatic C), 123.49 (aromatic C), 124.14 (aromatic C), 126.98 (aromatic C), 127.64 (aromatic C), 128.21 (aromatic C), 128.56 (aromatic C), 128.89 (aromatic C), 129.50 (aromatic C), 135.42 (aromatic C), 137.31 (N—CH—N imidazolium), 151.59 (aromatic C), 160.04 (aromatic C).

IR: 3123, 3071, 2919, 2850, 1634, 1552, 1468, 1381, 1248, 1154, 1097, 1061, 991, 869, 793, 768, 719, 693, 662, 620 cm$^{-1}$.

Example 11

1-Hexadecyl-3-[4-(5-phenyl-oxazol-2-yl)-benzyl]-3H-imidazol-1-ium hexadecyl sulphate, 2d

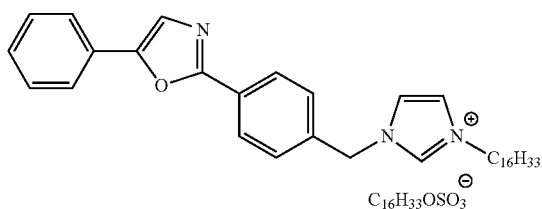

The experimental procedure is identical to the procedure for compound 2c (1-hexadecyl-3-[4-(5-phenykoxazol-2-yl)-benzyl]-3H-imidazol-1-ium bromide 1.010 g, 1.7 mmol, 60 mL EtOH), sodium hexadecyl sulphate (0.919 g, 2.7 mmol, 180 mL EtOH/60 mL H$_2$O).

C$_{51}$H$_{81}$N$_3$O$_5$S=848.27 g.mol$^{-1}$
Yield as colourless crystalline solid: (1.253 g, 89%)
Mp=130±1° C.
$^1$H NMR (300 MHz, CDCl$_3$, 20° C.): δ 10.04 ppm (s, 1H, N—CH—N imidazolium), 8.13 (d, 2H, aromatic =CH—, $^3$J=8.2 Hz), 7.71 (d, 2H, aromatic =CH—, $^3$J=7.4 Hz), 7.58 (d, 2H, aromatic =CH—, $^3$J=7.9 Hz), 7.46 (m, 3H, aromatic =CH—), 7.36 (m, 1H, aromatic =CH—), 7.19 (d, 2H, aromatic =CH—, $^3$J=11.0 Hz), 5.57 (s, 2H, Ph-CH$_2$—N), 4.25 (t, 2H, N—CH$_2$—(CH$_2$)$_{14}$—CH$_3$, $^3$J=7.4 Hz), 4.10 (t, 2H, CH$_3$—(CH$_2$)$_9$—CH$_2$—CH$_2$—OSO$_3^-$, $^3$J=6.9 Hz), 1.90 (m, 2H, N—CH$_2$—CH$_2$—(CH$_2$)$_{13}$—CH$_3$), 1.68 (m, 2H, CH$_3$—(CH$_2$)$_9$—CH$_2$—CH$_2$—OSO$_3^-$), 1.24 (m, 52H, N—CH$_2$—CH$_2$—(CH$_2$)$_{13}$—CH$_3$) and CH$_3$—(CH$_2$)$_{13}$—CH$_2$—CH$_2$—OSO$_3^-$), 0.88 (m, 6H, N—CH$_2$—CH$_2$—(CH$_2$)$_{13}$—CH$_3$) and CH$_3$—(CH$_2$)$_{13}$—CH$_2$—CH$_2$—OSO$_3^-$, $^3$J=6.6 Hz)
$^{13}$C {$^1$H} NMR (75 MHz, CDCl$_3$, 20° C.): δ 14.04 (N—(CH$_2$)$_{15}$—CH$_3$) and CH$_3$—(CH$_2$)$_{15}$—OSO$_3^-$) ppm, 22.61 (N—(CH$_2$)$_{14}$—CH$_2$—CH$_3$) and CH$_3$—CH$_2$—(CH$_2$)$_{14}$—OSO$_3^-$), 25.93 (N—(CH$_2$)$_{13}$—CH$_2$—CH$_2$—CH$_3$) and CH$_3$—CH$_2$—CH$_2$—(CH$_2$)$_{13}$—OSO$_3^-$), 26.24 (N—(CH$_2$)$_{12}$—CH$_2$—(CH$_2$)$_2$—CH$_3$) and CH$_3$—(CH$_2$)$_2$—CH$_2$—(CH$_2$)$_{12}$—OSO$_3^-$), 28.94 (N—(CH$_2$)$_2$—(CH$_2$)$_{10}$—(CH$_2$)$_3$—CH$_3$) and CH$_3$—(CH$_2$)$_3$—(CH$_2$)$_{10}$—(CH$_2$)$_2$OSO$_3^-$), 29.29 (N—(CH$_2$)$_2$—(CH$_2$)$_{10}$—(CH$_2$)$_3$—(CH$_3$) and CH$_3$—(CH$_2$)$_3$—(CH$_2$)$_{10}$—(CH$_2$)$_2$—OSO$_3^-$), 29.37 (N—(CH$_2$)$_2$—(CH$_2$)$_{10}$—(CH$_2$)$_3$—CH$_3$) and CH$_3$—(CH$_2$)$_3$—(CH$_2$)$_{10}$—(CH$_2$)$_2$—OSO$_3^-$), 29.43 (N—(CH$_2$)$_2$—(CH$_2$)$_{10}$—(CH$_2$)$_3$—CH$_3$) and CH$_3$—(CH$_2$)$_3$—(CH$_2$)$_{10}$—(CH$_2$)$_2$—OSO$_3^-$), 29.48 (N—(CH$_2$)$_2$—(CH$_2$)$_{10}$—(CH$_2$)$_3$—CH$_3$) and CH$_3$—(CH$_2$)$_3$—(CH$_2$)$_{10}$—(CH$_2$)$_2$—OSO$_3^-$), 29.64 (N—(CH$_2$)$_2$—(CH$_2$)$_{10}$—(CH$_2$)$_3$—CH$_3$) and CH$_3$—(CH$_2$)$_3$—(CH$_2$)$_{10}$—(CH$_2$)$_2$—OSO$_3^-$), 30.06 (CH$_3$—(CH$_2$)$_9$—CH$_2$—CH$_2$—OSO$_3^-$), 31.86 (N—CH$_2$—CH$_2$—(CH$_2$)$_{13}$-CH$_3$), 50.15 (CH$_3$—(CH$_2$)$_9$—CH$_2$—CH$_2$—OSO3$^-$), 52.74 (N—CH$_2$—CH$_2$—(CH$_2$)$_{14}$-CH$_3$), 67.73 (Ph-CH$_2$—N), 122.00 (aromatic C), 122.23 (aromatic C), 123.48 (aromatic C), 124.14 (aromatic C), 126.98 (aromatic C), 127.64 (aromatic C), 128.20 (aromatic C), 128.56 (aromatic C), 128.89 (aromatic C), 129.49 (aromatic C), 135.40 (aromatic C), 137.31 (N—CH—N imidazolium), 151.59 (aromatic C), 160.04 (aromatic C).

IR: 3123, 3071, 2918, 2850, 1630, 1552, 1470, 1409, 1381, 1248, 1153, 1113, 1063, 987, 872, 845, 793, 769, 719, 693, 662, 620 cm$^{-1}$.

Example 12

Thermal stability of 1-alkyl-3-[4-(5-phenyl-oxazol-2-yl)-benzyl]-3H-imidazol-1-ium bromide

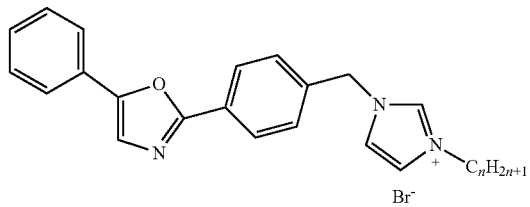

The thermal stability of the 1-alkyl-3-[4-(5-phenyl-oxazol-2-yl)-benzyl]-3H-imidazol-1-ium bromide compounds was investigated by performing thermogravimetric analysis (TGA-DSC) using "SDT Q600" apparatus by TA Instruments, equipped with a DSC-TGA Standard module. Analyses were conducted under purging with air at 50.0 ml/mn in a platinum pan at a rate of 10° C./mn.

TABLE 1

| Alkylimidazolium bromide (n) | $T_{dec}$ (° C.) |
| --- | --- |
| n = 1 | 200-205 |
| n = 6 | 190-200 |
| n = 8 | 200-210 |
| n = 10 | 190-200 |
| n = 12 | 200-210 |
| n = 14 | 190-200 |
| n = 16 | 210-220 |

Example 13

Transition Temperature

The 1-alkyl-3-[4-(5-phenyl-oxazol-2-yl)-benzyl]-3H-imidazol-1-ium bromide radioluminophores were characterized by differential scanning calorimetry using "DSC Q1000" apparatus by TA Instruments, equipped with a DSC Standard cell and RCS crysostat. Analyses were conducted under purging with nitrogen at 50.0 ml/mn in an aluminium pan at different rates.

The results obtained are shown FIG. 1. They illustrate the modular nature of the physical properties of the formula (I) compounds. In addition, and interestingly, a liquid crystal mesophase is observed with the molecule having a $C_{16}$ carbon chain. The mesomorph properties were characterized by microscope observations under polarized light. The emergence of the liquid-crystal phase on cooling the compound from the liquid state (isotropic) is characteristic of a smectic-A phase (formation of rods with positive units). Differential calorimetry indicates crystal-mesomorph transition at 97° C. (enthalpy 11.9 J/g) and a mesomorph-liquid transition (clarification point) at 115° C. (2.0 J/g).

Example 14

Detecting Property n-γ discrimination is based on the comparison, fast components being equal, between slow components resulting from ionization processes respectively induced by gamma rays and recoil protons produced by neutrons [6-11]. The most fine-tuned means of measuring fluorescence decay is to excite the sample in pulses (nanosecond pulse) and statistically to reconstitute its response using a coincidence technique, using a photomultiplier with single photoelectron operation.

The initial measurements of decay excited by nanosecond pulsed protons of energy lying between 1 and 4 MeV (4 MV electrostatic accelerator) were performed under conditions for producing a recoil proton to induce detector response. As an example, FIGS. 2 to 4 give curves of fluorescence decay obtained with the compounds of Examples 7 (FIG. 1), 8 (FIGS. 2) and 9 (FIG. 3) ($C_{16}$ alkyl chains) excited by Co60 photons and protons of 2 MeV. The presence of two components, fast (t<20 ns; t: time)) and slow (t≧20 ns) can be clearly seen. The fast component is of exponential type. The lifetime of the excited fluorescent state of the compound lies between one and two nanoseconds. As predicted by theory, the decay law for the slow component is of type t 3/2, which indicates isotropic diffusion of the charge carriers before their mutual recombination. The behaviour of these novel molecules, with respect to detection, is therefore fully similar to that of former products and can therefore replace these products without requiring any major modification to detection systems (photomultiplier) and data acquisition systems (electronics and computerized processing).

Example 15

Absorption and Emission Spectra

It was also observed that the fluorescence emission of the $C_{16}$ compound in Example 7 indeed lies in the ultraviolet spectral region, at around 400 nm (see emission and absorption spectra in FIG. 5), which is fully compatible with the replacement of current scintillators without modifying detection and analysis chains.

Example 16

Resistance to Radiation

The decrease in fluorescence intensity resulting from damage inflicted upon materials by protons of 2 MeV was also investigated. The molecules of the invention were observed to exhibit very good behaviour (see FIG. 6) if their resistance is compared with that of competing materials such as BC418 marketed by Bicron, a subsidiary of Saint-Gobain. Therefore, for a given fluorescence intensity at zero fluence, it is observed that loss in intensity of the $C_{16}$ compound in Example 7 with fluence is not very different from that of BC418.

Example 17 n-γ Discriminating Property

The neutron gamma discriminating property of the compound in Example 9 was tested under real conditions from a radioactive source of sodium and cobalt 60 ($^{22}$Na+$^{60}$Co) and of americium-beryllium (AmBe). Analysis of the fast and slow components of fluorescence decay allowing tracing of the graph showing the signal integral (Q tot) along the abscissa, and the slow component integral (Q slow) along the ordinate. A very marked difference is observed between the intensity of the slow component obtained with gamma radiation (FIG. 7) and that obtained with neutrons (FIG. 8). This indisputably evidences the neutron gamma discriminating property of the formula (I) compounds.

Example 18

Methyl Methacrylate Polymer Containing 52% (By Weight) of Hexafluorophosphate Salt.

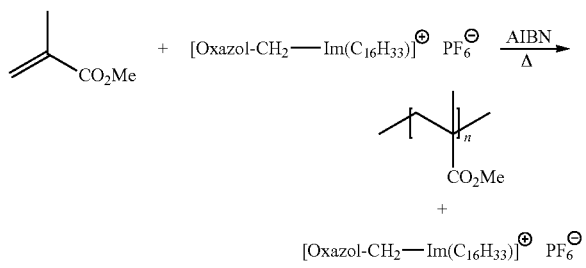

To a glass receptacle are added 1-hexadecyl-3-[4-(5-phenyl-oxazol-2-yl)-benzyl]-3H-imidazol-1-ium hexafluorophosphate (5.10 g, 8.4 mmol) and methyl methacrylate (MMA, Prolabo) (10.45 mL, 9.80 g, 98.0 mmol). The mixture is heated between 40° and 60° C. until the hexafluorophosphate salt has completely dissolved. 2'-Azobis(2-methylpropionitrile) (AIBN, Acros, 12 mg) is then added. The mixture is heated at different temperatures ($T_i$: ° C.) for different periods of time ($t_i$: hours).

1/ ($T_1, t_1$): (60, 3)
2/ ($T_2, t_2$): (96, 1)
3/ ($T_3, t_3$): (108, 2)

After these times, to complete the polymerization process, the mixture is heated to 115° C. for 10-30 mn. The mixture is then cooled over an ice bath (0° C.) for 20 mn. The polymer of methyl methacrylate incorporating the hexafluorophosphate salt (52% by weight) is a transparent solid.

| Experiment n° | Wt %, (salt: g/MMA: g) | AIBN (mg) | $T_1, T_2, T_3$ (° C.) | $t_1, t_2, t_3$ (h) |
|---|---|---|---|---|
| EB083 | 0 (0/2.817) | 8 | 60, 96, 108 | 2.5, 3, 0 |
| EB095 | 11 (0.10/0.939) | 4 | 60, 96, 115 | 3, 0, 3 |
| EB096 | 21 (0.20/0.939) | 4 | 60, 96, 108 | 3, 3.5, 0 |
| EB097 | 43 (0.20/0.469) | 2 | 60, 96, 108 | 3, 4, 0 |
| EB099 | 43 (0.20/0.469) | 2 | 60, 96, 115 | 3, 2.5, 1 |
| EB100 | 43 (0.20/0.469) | 2 | 60, 96, 108 | 3, 2, 2 |
| EB101 | 53 (0.25/0.469) | 2 | 60, 96, 108 | 3, 1.5, 2 |
| EB102 | 64 (0.30/0.469) | 3 | 60, 96, 108 | 3, 1, 2 |
| EB103 | 75 (0.35/0.469) | 3 | 60, 96, 108 | 3, 1, 2.5 |

It is to be noted that the methyl methacrylate was previously dried over $CaH_2$, purified by vacuum distillation and stored at −25° C.

AIBN was purified by recrystallization from methanol at 0° C.

REFERENCES

[1] H.-J. Meyer and T. Wolff, Chem. Euro. J., 2000, 15, 2809-2817: *Water-binding Solid Scintillators: Synthesis, Emission properties and test in 3H and 14C counting,*

[2] S. Khabnadideh, Z. Rezaei, A. Khalafi-Nezhad, R. Bahrinajafi, R. Mohamadi, A. A. Farrokhroz, *Bioorganic & Medicinal Chemistry Letters* 13 (2003) 2863-2865—*Synthesis of N-alkyated Derivatives of Imidazole as Antibacterial Agents*

[3] Jen-Yen Cheng and Yen-Ho Chu*, *Tetrahedron Letters* 47 (2006) 1575-1579,

[4] Martin Tosoni, Sabine Laschat*, and Angelika Baro., *Helvetica Chimica Acta* Vol. 87 (2004)

[5] Wang, Xixin; Zhao, Jianling; Yang, Hao; Chen, Wentao; Zhu, Zhijia. Department of Chemistry, Nanyang Teacher's College, Nanyang, Peop. Rep. China. Huaxue Shiji (2001), 23(5), 306-307. Publisher: Huagongbu Huaxue Shiji Xinsizhan, CODEN: HUSHDR ISSN: 0258-3283. Journal written in Chinese. CAN 136:279384 AN 2001:877665 CAPLUS

[6] J.-M. Jung, Thése de Doctorat de l'Université Louis Pasteur n°998, Strasbourg, 1991

[7] D. Paligoric, J. Klein, Int. J. Rad. Phys. Chem. 4 (1972) 359

[8] J. Klein, R. Voltz, Phys. Rev. Letters 36 (1976) 1214

[9] J. Klein, R. Voltz, Can. J. Chem. 55 (1977) 2102

[10] J. Klein, J. Chim. Phys. 80 (1983) 627

[11] G. Klein, R. Voltz, M. Schott, *Chem. Phys. Left.* 16 (1972) 340; id. 19 (1973) 391

The invention claimed is:

1. Method for detecting gamma, X, neutron, proton radiation, comprising the step of detecting the fluorescence of a fluorophore compound $F_1$ carrying an organic cationic group combined with a counter-anion, or else carrying an anionic group combined with an organic counter-cation, said cationic group or organic counter-cation comprising at least one heteroatom chosen from among N, S or P carrying a positive charge.

2. The method according to claim 1, wherein the fluorophore compound $F_1$ carries an organic cationic group combined with a counter-anion.

3. The method according to claim 2, wherein the organic cationic group is a heterocyclic group optionally substituted by one to three groups chosen from among $R^{1a}$, $R^{1b}$, $R^{1c}$ or $R^{25}$, or else the organic cationic group is a group (a), (b), (c) or (d):

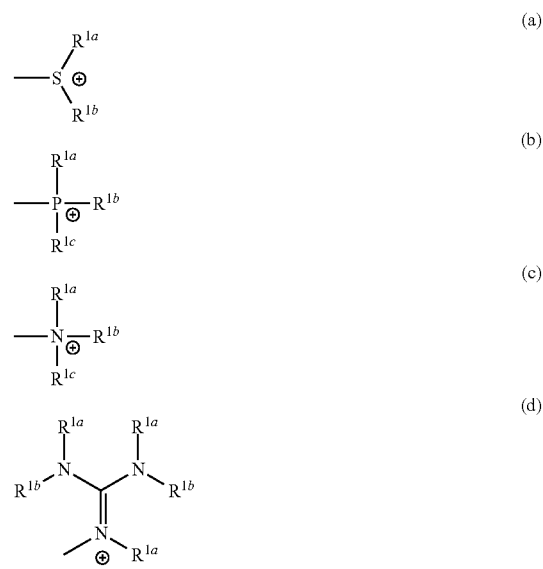

$R_{1a}$, $R_{1b}$, $R^{1c}$, on each occurrence, are each independently chosen from among H, $C_1$-$C_{30}$ alkyl, $C_3$-$C_7$ cycloalkyl, $C_6$-$C_{10}$ aryl, heteroaryl, arylalkyl, heteroarylalkyl groups, a fluorophore group $F_2$, wherein said alkyl, aryl or fluorophore $F_2$ groups are optionally substituted by 1 to 3 $R^{20}$ groups;

$R^{25}$ is independently chosen from among OH, $NH_2$, =O, $C(=O)OR^{21}$;

$R^{20}$, on each occurrence, is independently chosen from among F, Cl, Br, I, $OR^{22}$, $NR^{23}R^{24}$, NHOH, $NO_2$, CN, $CF_3$, $C_1$-$C_6$ alkyl, $C_2$-$C_6$ alkenyl, $C_2$-$C_6$ alkynyl, $C_6$-$C_{10}$ aryl, arylalkyl, =O, $C(=O)R^{22}$, $CO_2R^{22}$, $OC(=O)R^{22}$, $C(=O)NR^{23}R^{24}$, $OC(=O)NR^{23}R^{24}$, $NR^{21}C(=S)R^{22}$ and $S(O)_yR^{22}$;

$R^{21}$, on each occurrence, is independently chosen from among H or $C_1$-$C_6$ alkyl;

$R^{22}$, on each occurrence, is independently chosen from among H, $C_1$-$C_6$ alkyl, $C_6$-$C_{10}$ aryl and arylalkyl;

$R^{23}$ and $R^{24}$, on each occurrence, are independently chosen from among H, $C_1$-$C_6$ alkyl and $C_6$-$C_{10}$ aryl, or else $R^{23}$ and $R^{24}$ together with the hydrogen atom to which they are attached form a 3- to 7-membered heterocyclic group.

4. The method according to claim 3 of a compound of formula (A):

L*-Y—Z⁺X wherein:
Z⁺ is an organic caitonic group such as defined in claim 3,
X⁻ is an organic or inorganic anion,
Y is a $C_1$-$C_6$ alkylene group or:
   $(C_1$-$C_4$ alkylene$)_m$-Q-$(C_1$-$C_4$ alkylene$)_n$ group;
   $C_6$-$C_{10}$ arylene group;
wherein the alkylene, arylene groups are optionally substituted by 1 to 3 $R^{20}$ groups;
Q is a group from among —C(=O)—, —NR²¹C(=O)—, —C(=O)NR²¹—, —C(=O)O—, —OC(=O)—, —O—, —NR²¹—, —S(O)$_y$—, —CR²¹=CR²¹—, —C≡C—, $C_6$-$C_{10}$ arylene, 5-10-membered heteroarylene, $C_3$-$C_6$ cycloalkylene or 3- to 6-membered heterocycloalkylene,
wherein said arylene, heteroarylene, cycloalkylene groups are optionally substituted by 1 to 3 $R^{20}$ groups;
L* is a fluorophore group,
m is 0 or 1;
n is 0 or 1;
y is 0, 1 or 2,
The $R^{20}$ and $R^{21}$ groups being such as defined in claim 3.

5. The method according to claim 1, to discriminate between proton/gamma, proton/X, neutron/gamma, neutron/X, alpha/gamma, alpha/X, gamma ion/X ion radiation.

6. The method according to claim 1, wherein the organic cationic group is a heterocyclic group comprising at least one nitrogen atom.

7. The method according to claim 1, wherein the organic cationic group is a group chosen from among pyridil, imidazolyl, imidazolidinyl, oxazolyl, oxazolidinyl, thiazolyl, thiazolidinyl, pyrazolyl, triazolyl, tetrazolyl, benzotriazolyl, benzotriazolyle a guanine group, a caprolactam group.

8. The method according to claim 1, wherein the fluorophore compound $F_1$ carrying a cationic or anionic group is an oxazolyl, oxadiazolyl anthracenyl, phenanthrenyl radical.

9. The method according to claim 1, wherein the fluorophore compound F1 of formula (I):

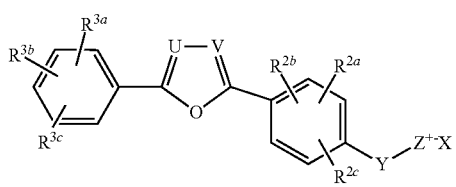

wherein:
U, V independently represent $CR^{26}$ or N, provided that at least one of U or V represents N;
$R^{26}$ is H, $C_1$-$C_6$ alkyl, $OR^{22}$, $NR^{23}R^{24}$, $NO_2$, C(=O)$R^{22}$, $CO_2R^{22}$, OC(=O)$R^{22}$, C(=O)$NR^{23}R^{24}$, OC(=O)$NR^{23}R^{24}$, $SO_3H$, $PO_oH$, CN;
$R^{2a}$, $R^{2b}$, $R^{2c}$, $R^{3a}$, $R^{3b}$, $R^{3c}$, on each occurrence, are independently chosen from among H, $C_1$-$C_{30}$ alkyl, $C_3$-$C_7$ cycloalkyl, $C_6$-$C_{10}$ aryl, heteroaryl, arylalkyl, heteroarylalkyl groups, wherein said alkyl or aryl groups are optionally substituted by 1 to 3 $R^{20}$ groups;
Y, Z⁺, X⁻, $R^{20}$, $R^{22}$, $R^{23}$, $R^{24}$ being such as defined in claim 3.

10. The method according to claim 9, wherein the compound of formula (A) is of formula (Ia):

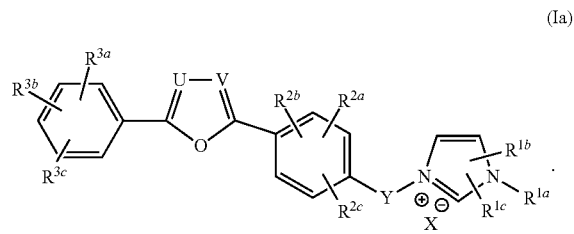

11. The method according to claim 1, comprising a step of manufacture of radar and industrial or medical dosimetry instruments, with a fluorophore compound according to claim 1.

12. Fluorophore compound $F_1$ carrying an organic cation group combined with a counter-anion, or else carrying an anionic group combined with an organic counter-cation, said cationic group or counter-cation comprising at least one heteroatom chosen from among N, S or P carrying a positive charge, wherein the fluorophore group $F_1$ is not an anthracenyl group.

13. The compound according to claim 12, wherein the fluorophore group is chosen from among an oxazolyl, oxadiazolyl or phenanthrenyl radical.

14. The compound according to claim 13, wherein the fluorophore group $F_1$ is an oxazolyl radical.

15. The compound of formula (I) according to claim 14:

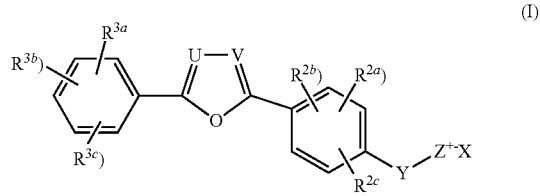

wherein Z⁺, X⁻, Y, U, V, $R^{2a}$, $R_{2b}$, $R_{2c}$, $R_{3a}$, $R_{3b}$, $R^{3c}$ are all such as defined in claim 9.

16. The compound of formula (I) according to claim 15, characterized in that it meets formula (Ia):

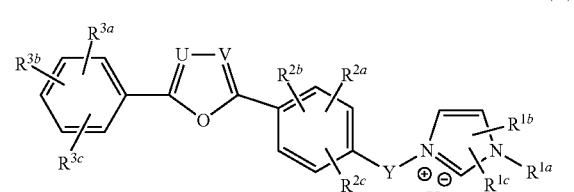

wherein $X^-$, $Y, U, V, R2a$, $R_{2b}$, $R^{2b}$, $R_{2c}$, $R^{3a}$, $R_{3b}$, $R_{3c}$ are such as defined in claim 15 and $R^{1a}$, $R_{1b}$, $R^{1c}$ are such as defined in claim 1.

17. The compound of formula (I) according to claim 16, wherein $R^{1a}$ is a $C_1$-$C_{16}$ alkyl group.

18. The compound of formula (I) according to claim 17, wherein $R^{1b}$ and $R^{1c}$ are both H.

19. Method for preparing a compound of formula (Ia) comprising the reaction of a compound of formula (II) with a compound of formula (III):

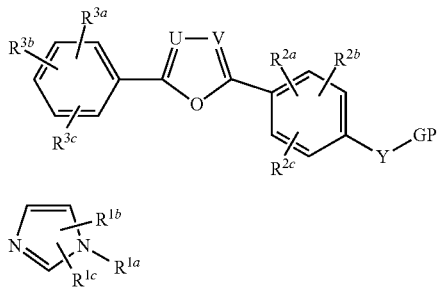

wherein $R^{1a}, R^{1b}, R^{1c}, R^{2a}, R^{2b}, R^{2c}, R^{3a}, R^{3b}, R^{3c}, U, Y$ are such as defined in claim 16 and GP represents a leaving group.

20. The compound according to claim 12, wherein U is $CR^{26}$.

21. The compound according to claim 20, wherein U is CH.

22. The compound according to claim 12, wherein Y is a $C_1$-$C_6$ alkylene group.

23. The compound according to claim 22, wherein Y is $CH_2$.

24. The compound of formula (I) according to claim 12, wherein $X^-$ is an anion chosen from among a halide, $P(R^4)_6^-$, $B(R^4)_4^-$, $SCN^-$, $(R^5SO_2)_2N^-$, $R^5OSO_3^-$, $R^5SO_3^-$, carborane, carbonate, hydrogenocarbonate, alcoholate, carboxylate, amide, phosphate, $SiF_6^-$, $SbF_6^-$, $I_3^-$, nitrate, halide oxide, silicate, sulphate, sulphonate, cyanide, carbanion or metallate, wherein:

$R^4$, on each occurrence, is a group independently chosen from among a halogen atom, $C_1$-$C_6$ alkyl group, $C6$-$C_{10}$ aryl group, arylalkyl group;

$R^5$, on each occurrence, is a group independently chosen from among $C_1$-$C_{20}$ alkyl, $C_1$-$C_{20}$ halogenoalkyl, $C_6$-$C_{10}$ aryl, arylalkyl.

25. The compound according to claim 12, wherein $X^-$ is chosen from among Br, $PF_6^-$, $BF_4^-$, $(CF_3SO_2)_2N^-$, $C_{12}H_{25}OSO_3^-$, $C_{16}H_{33}OSO_3^-$, $CF_3SO_3^-$.

26. The compound according to claim 12, chosen from among:
   1-methyl-3-[4-(5-phenyl-oxazol-2-yl)-benzyl]-3H-imidazol-1-ium bromide,
   1-hexyl-3-[4-(5-phenyl-oxazol-2-yl)-benzyl]-3H-imidazol-1-ium bromide,
   1-octyl-3-[4-(5-phenyl-oxazol-2-yl)-benzyl]-3H-imidazol-1-ium bromide,
   1-decyl-3-[4-(5-phenyl-oxazol-2-yl)-benzyl]-3H-imidazol-1-ium bromide,
   1-dodecyl-3-[4-(5-phenyl-oxazol-2-yl)-benzyl]-3H-imidazol-1-ium bromide,
   3-[4-(5-phenyl-oxazol-2-yl)-benzyl]-1-tetradecyl-3H-imidazol-1-ium bromide,
   1-hexadecyl-3-[4-(5-phenyl-oxazol-2-yl)-benzyl]-3H-imidazol-1-ium bromide,
   1-hexadecyl-3-[4-(5-phenyl-oxazol-2-yl)-benzyl]-3H-imidazol-1-ium hexafluorophosphate,
   1-hexadecyl-3-[4-(5-phenyl-oxazol-2-yl)-benzyl]-3H-imidazol-1-ium bis(trifluoromethylsulphonyl)imide,
   1-hexadecyl-3-[4-(5-phenyl-oxazol-2-yl)-benzyl]-3H-imidazol-1-ium dodecyl sulphate,
   1-hexadecyl-3-[4-(5-phenyl-oxazol-2-yl)-benzyl]-3H-imidazol-1-ium hexadecyl sulphate.

27. Material comprising a fluorophore compound according to claim 12.

28. The material according to claim 27, characterized in that it is a transparent plastic material.

* * * * *